(12) United States Patent
Ootsuki et al.

(10) Patent No.: US 10,993,838 B2
(45) Date of Patent: May 4, 2021

(54) IMAGE PROCESSING DEVICE, IMAGE PROCESSING METHOD, AND IMAGE PROCESSING PROGRAM

(71) Applicant: Sony Corporation, Tokyo (JP)

(72) Inventors: Tomoyuki Ootsuki, Kanagawa (JP); Tatsumi Sakaguchi, Kanagawa (JP); Junichiro Enoki, Kanagawa (JP); Yoshio Soma, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/609,564

(22) PCT Filed: Mar. 19, 2018

(86) PCT No.: PCT/JP2018/010738
§ 371 (c)(1),
(2) Date: Oct. 30, 2019

(87) PCT Pub. No.: WO2018/207466
PCT Pub. Date: Nov. 15, 2018

(65) Prior Publication Data
US 2020/0146885 A1    May 14, 2020

(30) Foreign Application Priority Data
May 9, 2017 (JP) .............................. JP2017-092978

(51) Int. Cl.
*A61F 9/00* (2006.01)
*A61F 9/007* (2006.01)
(Continued)

(52) U.S. Cl.
CPC .............. *A61F 9/007* (2013.01); *A61B 3/102* (2013.01); *A61F 9/00745* (2013.01);
(Continued)

(58) Field of Classification Search
CPC .. A61F 9/007; A61F 9/00745; A61F 9/00781; A61B 3/102; G06K 9/00597
See application file for complete search history.

(56) References Cited

U.S. PATENT DOCUMENTS

| 5,098,426 A | * | 3/1992 | Sklar ....................... A61F 9/008 606/5 |
| 2009/0163898 A1 | * | 6/2009 | Gertner .................. A61B 3/113 606/4 |

(Continued)

FOREIGN PATENT DOCUMENTS

| JP | 2016-073409 A | 5/2016 |
| JP | 2016-532483 A | 10/2016 |
| WO | 2017/065018 A1 | 4/2017 |

OTHER PUBLICATIONS

International Search Report and Written Opinion dated Jun. 19, 2018 for PCT/JP2018/010738 filed on Mar. 19, 2018, 12 pages including English Translation of the International Search Report.

(Continued)

Primary Examiner — Mishawn N. Hunter
(74) Attorney, Agent, or Firm — Xsensus LLP

(57) ABSTRACT

[Object] To provide an image processing device, an image processing method, and an image processing program that make it possible to perform an appropriate operation according to a procedure.
[Solving Means] An image processing device according to the present technology includes: an image recognition section that performs an image recognition with respect to a front image that is a captured image of an eye; a display information generator that generates display information; and a controller that controls at least one of a cross-sectional information acquisition section or the display information generator according to a selected procedure, the cross- (Continued)

sectional information acquisition section acquiring cross-sectional information regarding a cross section of an eye.

19 Claims, 33 Drawing Sheets

(51) Int. Cl.
    *A61B 3/10*      (2006.01)
    *G06K 9/00*      (2006.01)

(52) U.S. Cl.
    CPC ...... *A61F 9/00781* (2013.01); *G06K 9/00597* (2013.01); *G06K 2209/057* (2013.01)

(56) References Cited

U.S. PATENT DOCUMENTS

| | | | |
|---|---|---|---|
| 2012/0184846 A1 | 7/2012 | Izatt et al. | |
| 2015/0335480 A1* | 11/2015 | Alvarez | A61B 3/13 606/130 |
| 2015/0342698 A1* | 12/2015 | Eslami | A61B 90/361 606/130 |
| 2016/0143778 A1* | 5/2016 | Aljuri | A61B 34/25 606/6 |
| 2016/0331227 A1* | 11/2016 | Fingler | A61B 3/0083 |
| 2016/0331584 A1 | 11/2016 | Ren et al. | |
| 2018/0299658 A1* | 10/2018 | Carrasco-Zevallos | G02B 21/22 |

OTHER PUBLICATIONS

Roodaki, H., et al., "Introducing Augmented Reality to Optical Coherence Tomography in Ophthalmic Microsurgery," 2015 IEEE International Symposium on Mixed and Augmented Reality (ISMAR), IEEE, 2015, 6 pages.

\* cited by examiner

| Surgical technique | Procedure Mode | Procedure Mode | Procedure Mode | Procedure Mode | Procedure Mode | Procedure Mode |
|---|---|---|---|---|---|---|
| Start surgery | Step 1<br>0-1 | Step 2<br>0-2 | | | | ... |
| PEA | Creation of wound<br>1-1 | Incision of anterior capsule<br>1-2 | Formation of incision<br>1-3 | Division of nucleus<br>1-4 | Aspiration of nucleus<br>1-5 | ... |
| PPV ERM | PEA<br>Refer to PEA | Removal of vitreous body<br>2-2 | Membrane detachment<br>2-3 | | | |
| MIGS Device1 | PEA<br>Refer to PEA | Installation of device<br>3-2 | | | | |
| DSAEK | Creation of wound<br>4-1 | Insertion of graft<br>4-2 | Removal of space<br>4-3 | | | |
| ... | | | | | | |

FIG.5

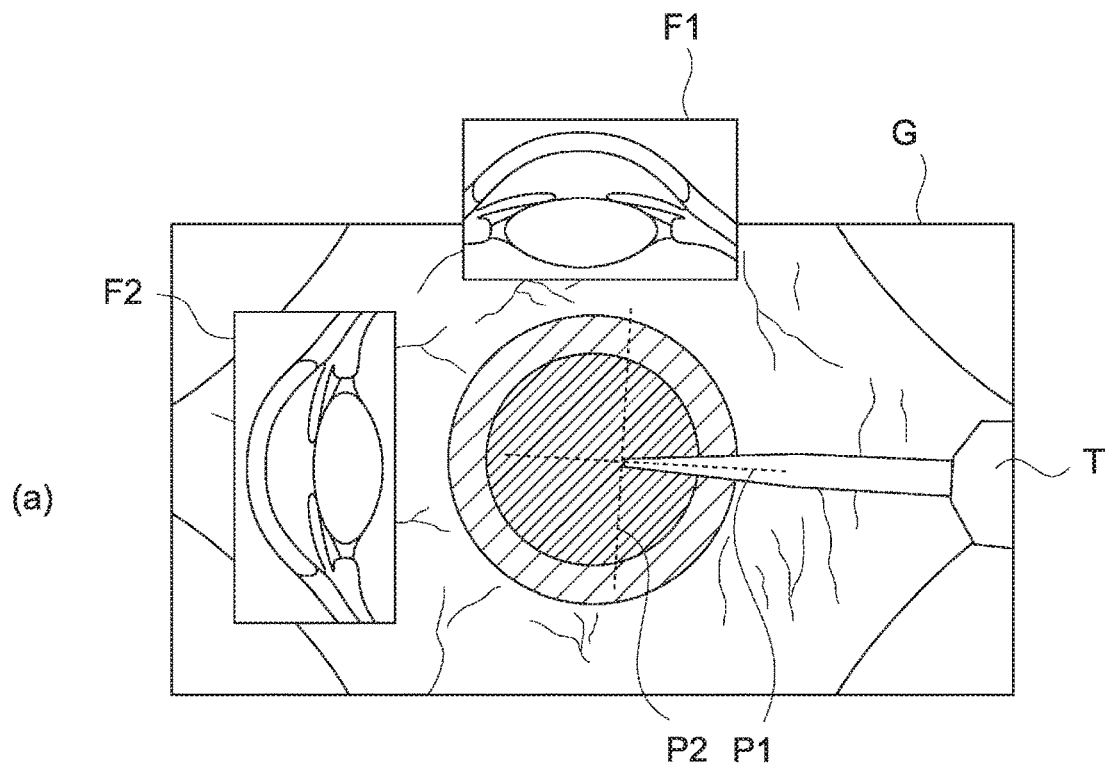
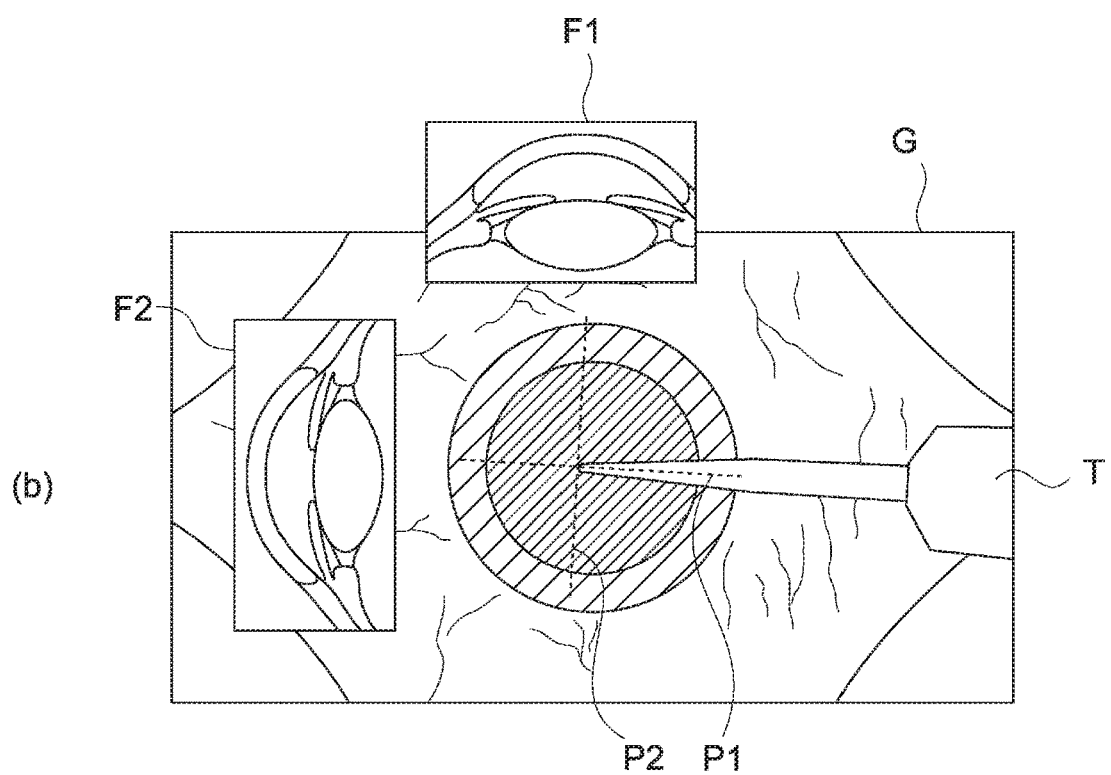
FIG.39

(a) 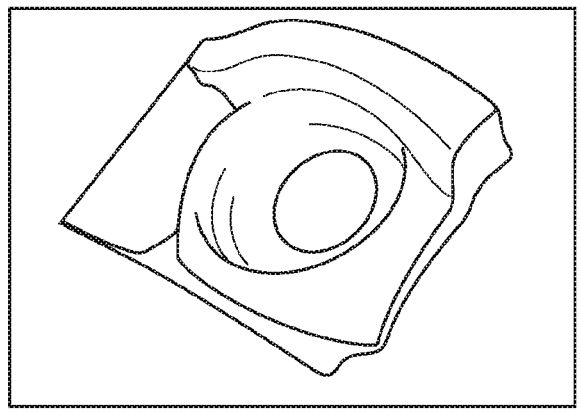
(b) 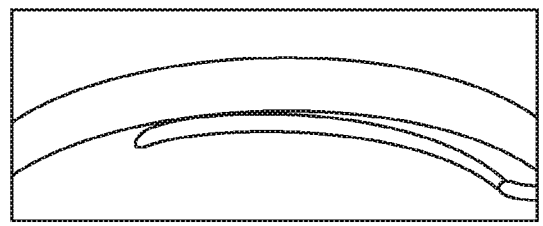
FIG.43

IMAGE PROCESSING DEVICE, IMAGE PROCESSING METHOD, AND IMAGE PROCESSING PROGRAM

CROSS-REFERENCE TO RELATED APPLICATIONS

The present application is based on PCT filing PCT/JP2018/010738, filed Mar. 19, 2018, which claims priority to JP 2017-092978, filed May 9, 2017, the entire contents of each are incorporated herein by reference.

TECHNICAL FIELD

The present technology relates to an image processing device, an image processing method, and an image processing program that can be used for ocular surgery.

BACKGROUND ART

In recent years, optical coherence tomography (OCT) has been increasingly used in eye-related surgery. The OCT is a technique that irradiates a surgical-target eye with near-infrared light, reconstructs a reflected wave due to respective ocular tissues, and generates an image, and this makes it possible to acquire cross-sectional information such as a cross-sectional image of a specific cross section (refer to, for example, Patent Literature 1).

It is often the case that surgery (such as Descemet's stripping automated endothelial keratoplasty) is constituted of a plurality of sequentially performed procedures (for example, after creating a wound, inserting a graft, and then removing a space), and in many cases, appropriate methods for acquiring and presenting cross-sectional information during surgery as well as an appropriate method for presenting a graphical user interface (GUI) related to treatment during surgery differ depending on a procedure.

CITATION LIST

Patent Literature

Patent Literature 1: Japanese Patent Application Laid-open No. 2016-73409

DISCLOSURE OF INVENTION

Technical Problem

In the surgery using the OCT described above, there is a need to appropriately select, depending on a procedure, methods for acquiring and presenting cross-sectional information as well as a method for presenting a GUI. Here, in general, the flow of procedure is often stylized depending on surgery, but conventionally, there is no option but to separately select a method for acquiring cross-sectional information, a method for presenting cross-sectional information, or a method for presenting a GUI. Further, its selection procedure is complicated since the flow of procedure is not considered, and thus, overall, it takes much time and effort for a user to perform the selection procedure. Furthermore, regarding some surgeries or procedures, there are no appropriate methods for acquiring and presenting cross-sectional information as well as for presenting a GUI.

In view of the circumstances described above, it is an object of the present technology to provide an image processing device, an image processing method, and an image processing program that make it possible to perform an appropriate operation according to a procedure.

Solution to Problem

In order to achieve the object described above, an image processing device according to an embodiment of the present technology includes: an image recognition section that performs an image recognition with respect to a front image that is a captured image of an eye; a display information generator that generates display information; and a controller that controls at least one of a cross-sectional information acquisition section or the display information generator according to a selected procedure, the cross-sectional information acquisition section acquiring cross-sectional information regarding a cross section of an eye.

According to this configuration, it is possible to help an operator perform a treatment since the image processing device operates in an operation mode according to a procedure, and cross-sectional information is acquired, or cross-sectional information is presented, or a GUI is presented.

The controller may select a procedure in response to an instruction given by a user.

The instruction by the user may be an instruction given using a manipulation device such as a foot switch, or an instruction given using a position of a surgical tool in a field of view of the image image-capturing device, as described later.

The controller may select a procedure according to an instruction given by a user and a state recognition performed with respect to the front image that is a captured image of an eye.

In addition to the instruction given by the user, the controller can select a procedure according to the state recognition using characteristics of the front image or a result of an image recognition. For example, when a surgical technique is designated by the user, the controller can select a procedure included in the surgical technique according to the state recognition.

The controller may select a procedure according to a state recognition performed with respect to the front image that is a captured image of an eye.

The controller can also select a procedure only using the state recognition.

The controller may determine the instruction given by the user using a result of a recognition performed by the image recognition section.

According to this configuration, a user can cause the controller to select a procedure by performing a specified operation in the field of view in the front image, and thus there is no need to manipulate an input device, which results in an improvement in usability. The configuration is particularly advantageous in that it becomes possible to perform selection without letting go of a surgical tool, in addition to there being no need to touch a dirty region.

The controller may perform a state recognition using a result of a recognition performed by the image recognition section.

The controller can perform the state recognition according to the result of the recognition (a surgical tool and a site of an eye that are included in the front image) performed by the image recognition section, and can select a procedure.

The image recognition section may recognize a surgical tool included in the front image, and the controller may determine the instruction given by the user according to a position of a tip of the surgical tool included in the front image.

According to this configuration, the user can designate a procedure by moving the surgical tool to a specified position in the field of view in the front image.

The image recognition section may recognize a surgical tool included in the front image, and the controller may specify a type of the surgical tool included in the front image, and may perform the state recognition according to the type of the surgical tool.

According to this configuration, the controller can select a procedure in which a surgical tool is used, by the user causing the surgical tool to enter the field of view in the front image.

The controller may perform the state recognition according to the type of the surgical tool and characteristics of the front image.

The controller can specify a surgical technique according to the characteristics of the front image (such as a distribution of brightness), and can select a procedure included in the surgical technique according to the type of the surgical tool.

The image recognition section may recognize a surgical tool included in the front image, and the controller may determine a cross-sectional position according to a shape of the surgical tool included in the front image, the cross-sectional position being a position of a cross section for which cross-sectional information is to be acquired.

The controller can determine the cross-sectional position on the basis of the shape of the surgical tool (for example, in the longitudinal direction of the surgical tool). A specific cross-sectional position with respect to the surgical tool can be set according to a procedure.

The image recognition section recognizes a site of an eye that is included in the front image, and the controller determines a cross-sectional position according to the site of an eye included in the front image, the cross-sectional position being a position of a cross section for which cross-sectional information is to be acquired.

The controller can determine the cross-sectional position on the basis of a site of an eye (for example, a cornea's center). A specific cross-sectional position with respect to the site of an eye can be set according to a procedure.

The image recognition section may recognize a surgical tool and a site of an eye that are included in the front image, and the controller may determine a cross-sectional position according to a shape of the surgical tool included in the front image and the site of an eye included in the front image, the cross-sectional position being a position of a cross section for which cross-sectional information is to be acquired.

The controller can determine the cross-sectional position on the basis of a shape of a surgical tool and a site of an eye (for example, a line connecting a cornea's center to a tip of the surgical tool). A specific cross-sectional position with respect to the surgical tool and the site of an eye can be set according to a procedure.

The display information generator may generate the display information including the cross-sectional information acquired by the cross-sectional information acquisition section, and may change a position of the cross-sectional information in the display information according to a cross-sectional position that is a position of a cross section for which cross-sectional information is to be acquired.

According to this configuration, it is possible to present, to a user, display information in which cross-sectional information is arranged at a specified position according to a procedure.

The display information generator may generate the display information including the cross-sectional information acquired by the cross-sectional information acquisition section, and may change an orientation of the cross-sectional information in the display information according to an orientation of a cross section for which cross-sectional information is to be acquired.

According to this configuration, it is possible to present, to a user, display information in which cross-sectional information is arranged in a specified orientation according to a procedure.

The image recognition section may perform an image recognition with respect to the cross-sectional information, and the controller may detect an incision edge formed by a treatment performed according to a result of the image recognition performed by the image recognition section with respect to the cross-sectional information.

According to this configuration, it is possible to detect an incision edge of a less visible site of an eye (for example, an anterior capsule of a crystalline lens), and to present it to a user.

The image recognition section may recognize a site of an eye in the front image, the controller may specify a position of the incision edge in the front image according to the site of an eye detected by performing the image recognition, and the display information generator may generate display information obtained by superimposing an image at the position specified by the controller, the superimposed image including the incision edge.

According to this configuration, an image including a detected incision edge is superimposed to be displayed on a front image, and thus a user can grasp the detected incision edge referring to the front image.

The display information generator may generate display information obtained by superimposing an image on the front image, the superimposed image indicating an end point of a cross-sectional line indicating a position of a cross section for which cross-sectional information is to be acquired.

An image of a cross-sectional line is generally displayed when a cross-sectional position is indicated in a front image, and the image of the cross-sectional line may reduce the visibility of the front image. Thus, it is possible to present the cross-sectional line and to secure the visibility of the front image by superimposing, on the front image, an image (such as an arrow) indicating an end point of the cross-sectional line.

The display information generator may generate display information obtained by processing the front image to depict a cross-sectional line indicating a position of a cross section for which cross-sectional information is to be acquired.

According to this configuration, it is possible to present a cross-sectional line by processing a front image (for example, changing brightness and a saturation of color). The processing may be performed on a region corresponding to the cross-sectional line in the front image, or a region not corresponding to the cross-sectional line.

In order to achieve the object described above, an image processing method according to an embodiment of the present technology includes: performing, by an image recognition section, an image recognition with respect to a front image that is a captured image of an eye;
generating display information by a display information generator; and
controlling, by a controller, at least one of a cross-sectional information acquisition section or the display information generator according to a selected procedure, the cross-sectional information acquisition section acquiring cross-sectional information regarding a cross section of an eye.

In order to achieve the object described above, an image processing system according to an embodiment of the present technology includes a cross-sectional information acquisition device, a front image capturing device, and an image processing device.

The cross-sectional information acquisition device includes a cross-sectional information acquisition section that generates cross-sectional information regarding a cross section of an eye;

The front image capturing device includes a front image acquisition section that captures an image of an eye to generate a front image, and The image processing device includes an image recognition section, a display information generator, and a controller, the image recognition section performing an image recognition with respect to the front image, the display information generator generating display information, the controller controlling at least at least one of the cross-sectional information acquisition section or the display information generator according to a selected procedure.

Advantageous Effects of Invention

As described above, the present technology makes it possible to provide an image processing device, an image processing method, and an image processing program that make it possible to perform an appropriate operation according to a procedure. Note that the effect described here is not necessarily limitative and may be any effect described in the present disclosure.

BRIEF DESCRIPTION OF DRAWINGS

FIG. 5 is a table that is used by a controller of the information processing system and in which procedures are given that are performed in a surgical technique.

FIG. 39 schematically illustrates display information presented by the image processing system.

FIG. 43 schematically illustrates volume data acquired by the image processing system and a cross-sectional image generated from the volume data.

MODE(S) FOR CARRYING OUT THE INVENTION

An image processing system according to an embodiment of the present technology will be described.

[Configuration of Image Processing System]

Figure 1:
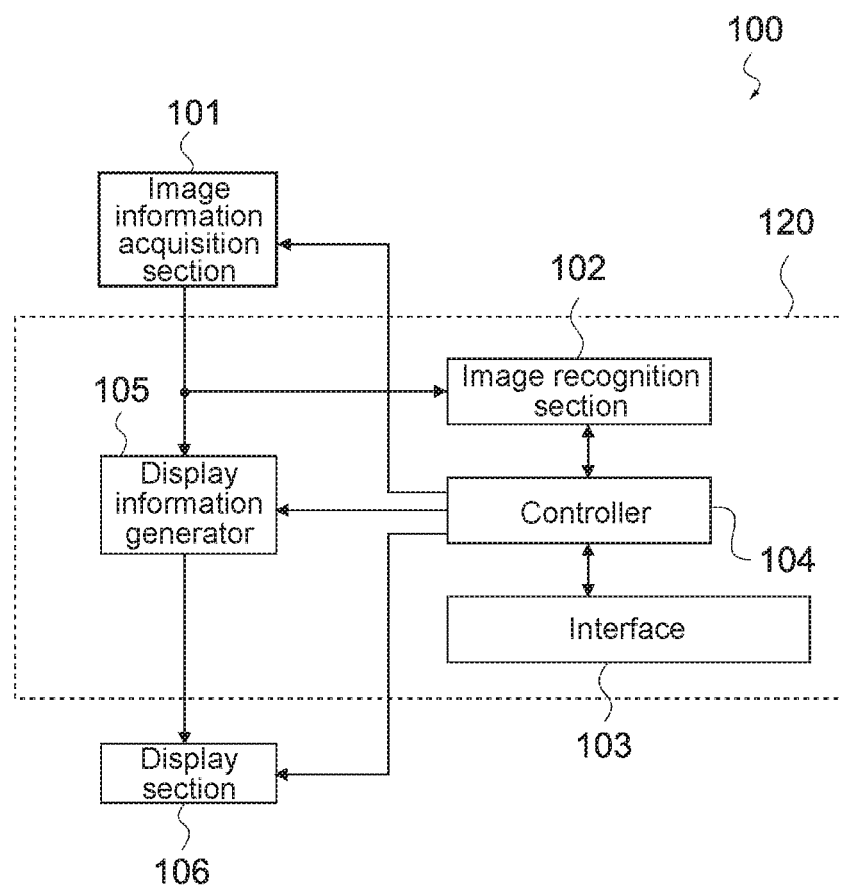
FIG. 1 schematically illustrates an image processing system according to an embodiment of the present technology.

FIG. 1 is a block diagram of a configuration of an image processing system 100 according to the present embodiment. As illustrated in the figure, the image processing system 100 includes an image information acquisition section 101, an image recognition section 102, an interface 103, a controller 104, a display information generator 105, and a display section 106. Further, the image recognition section 102, the interface 103, the controller 104, and the display information generator 105 constitute a functional configuration of an image processing device 120.

Figure 2:
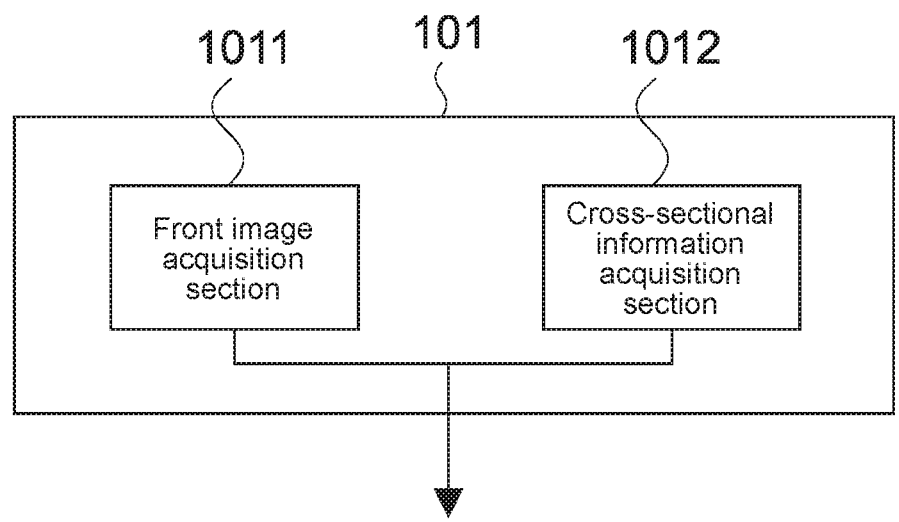
FIG. 2 schematically illustrates an image information acquisition section included in the image processing system.

The image information acquisition section 101 acquires image information regarding a treatment-target eye. FIG. 2 is a block diagram of a configuration of the image information acquisition section 101. As illustrated in the figure, the image information acquisition section 101 includes a front image acquisition section 1011 and a cross-sectional information acquisition section 1012.

The front image acquisition section 1011 includes an imaging element such as a charge-coupled device (CCD) or a complementary metal oxide semiconductor (CMOS), and an arbitrary optical system, and constitutes a functional configuration of a front-image capturing device that is capable of capturing an image of a treatment-target eye (hereinafter referred to as a front image) by being controlled by the controller 104.

The cross-sectional information acquisition section 1012 includes optical coherence tomography (OCT) or a Scheimpflug camera, and constitutes a functional configuration of a cross-sectional information acquisition device that is capable of capturing cross-sectional information regarding a cross section of a treatment-target eye by being controlled by the controller 104.

When the cross-sectional information acquisition device is OCT, the cross-sectional information acquisition section 1012 may acquire a cross-sectional image of a specified cross section, or may acquire, in advance and as volume data, cross-sectional information regarding a cross section of an eye in a wide range and may combine cross-sectional images of a position specified in the volume data. Further, the cross-sectional information acquisition section 1012 may acquire, as a moving image, successive cross-sectional images that are acquired for a certain period of time.

The image information acquisition section 101 provides the acquired front image and the acquired cross-sectional information to the image recognition section 102 and the display information generator 105.

The image recognition section 102 performs an image recognition process on image information (the front image or the cross-sectional information) acquired by the image information acquisition section 101. The image recognition section 102 is capable of recognizing an object image (such as an image of a surgical tool or a site of an eyeball) and an incision edge that are included in the image information, which will be described in detail later. The image recognition section 102 is capable of performing an image recognition using a method such as an edge detection or pattern matching, and its algorithm is not particularly limited. The image recognition section 102 provides a result of the recognition to the controller 104.

The interface 103 receives an input performed by a user or communicates with other surgical devices. The interface 103 provides acquired information to the controller 104.

The controller 104 controls each section. The controller 104 selects a procedure according to, for example, the input performed by the user or the result of the image recognition performed by the image recognition section 102, and controls the cross-sectional information acquisition section 1012 and the display information generator 105 in an operation mode depending on the selected procedure, which will be described in detail later.

The display information generator 105, for example, processes the image information provided by the image information acquisition section 101 in accordance with a control performed by the controller 104, and generates display information. For example, the display information generator 105 can generate display information by superimposing a menu or a cross-sectional position described later on a front image. The display information generator 105 provides the generated display information to the display section 106.

The display section 106 presents, to a user, the display information provided by the display information generator 105, by displaying the display information on a display device such as a display.

[Regarding Front Image and Cross-Sectional Image]

Figure 3:
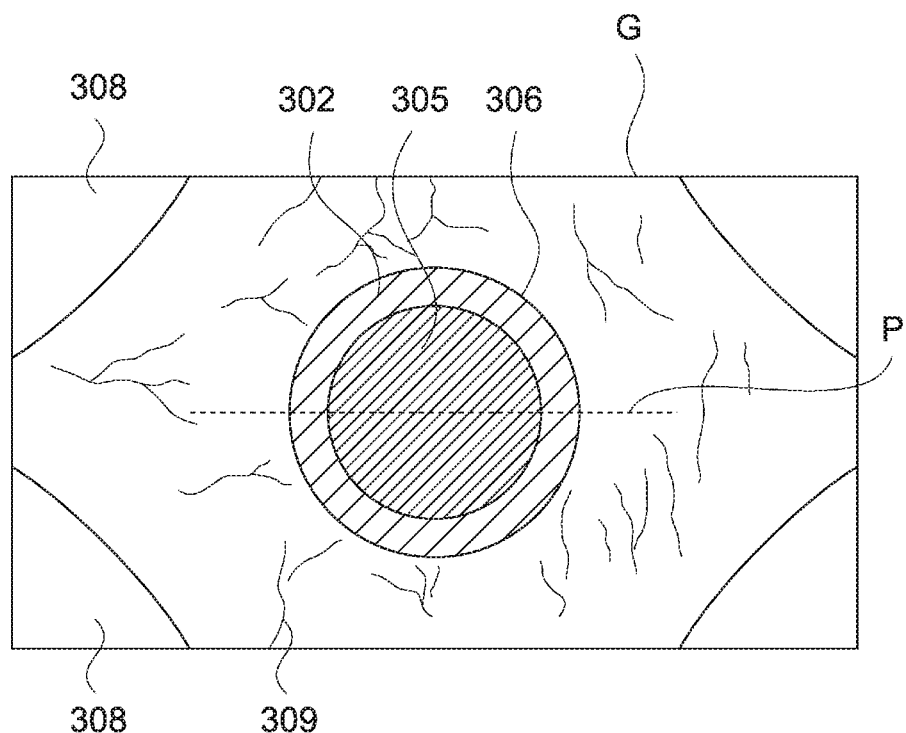
FIG. 3 illustrates an example of a front image acquired by a front image acquisition section of the image processing system.
Figure 4:
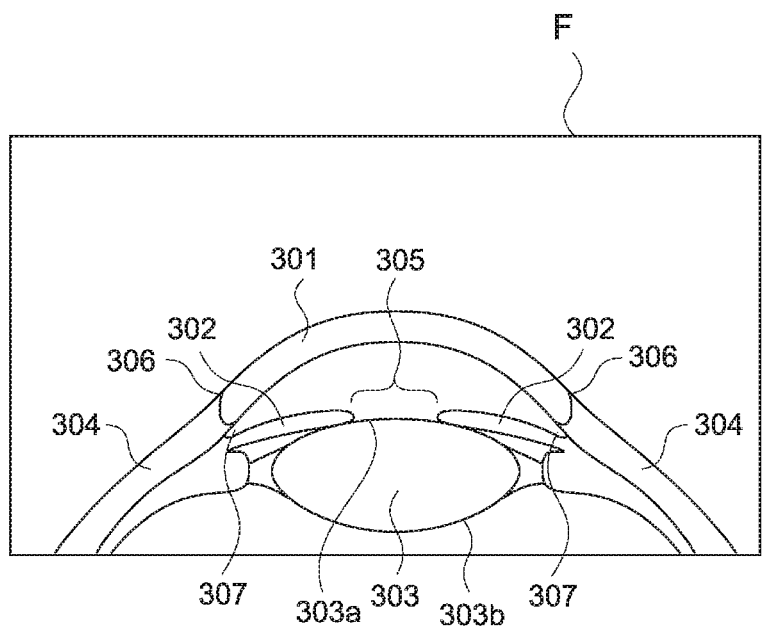
FIG. 4 illustrates an example of cross-sectional information acquired by a cross-sectional information acquisition section of the image processing system.

FIG. 3 illustrates an example of a front image acquired by the front image acquisition section 1011 (hereinafter referred to as a front image G), and FIG. 4 illustrates an example of a cross-sectional image acquired by the cross-sectional information acquisition section 1012 (hereinafter referred to as a cross-sectional image F). The cross-sectional image illustrated in FIG. 4 is an image acquired at a position of a cross section illustrated in FIG. 3 (hereinafter referred to as a cross-sectional position P).

As illustrated in the figures, an eyeball is constituted of tissues such as a cornea 301, an iris 302, a crystalline lens 303, and a sclera 304. A pupil 305 is a portion surrounded by the iris 302 on the surface of the crystalline lens 303, and a corneal limbus 306 is the periphery of the cornea 301. An iridocorneal angle 307 is situated at both ends of the cornea 301. A membranous anterior capsule 303a is situated on the front surface of the crystalline lens 303, and a membranous posterior capsule 303b is situated on the back surface of the crystalline lens 303. Further, as illustrated in FIG. 3, the front image G includes an eyelid 308 that is opened using an eye speculum, and blood vessels 309. Note that the cornea 301 is not illustrated in FIG. 3 since it is transparent.

[Operation of Image Processing System]

FIG. 5 is table in which the operation mode depending on the procedure of the image processing system 100, is given. As illustrated in the figure, examples of a surgical technique include phacoemulsification and aspiration (PEA), pars plana vitrectomy (PPV), removal of epi-retinal membrane (ERM), minimally invasive glaucoma surgery (MICS), installation of Device 1, and Descemet's stripping automated endothelial keratoplasty (DSAEK).

As illustrated in the figure, each surgical technique is constituted of a plurality of procedures. For example, in the case of the PEA, procedures of creating a wound (an opening for inserting a surgical tool) (1-1), incising an anterior capsule (1-2), forming an incision (1-3), dividing a nucleus (1-4), and aspirating the nucleus (1-5) are sequentially performed. Further, in the case of the removal of ERM in the PPV, the respective procedures of the PEA are performed, and then removal of a vitreous body (2-2) and membrane detachment (2-3) are sequentially performed. Note that the surgical techniques and the procedures described here are examples, and the image processing system 100 can also be used for other surgical techniques and procedures.

Figure 6:
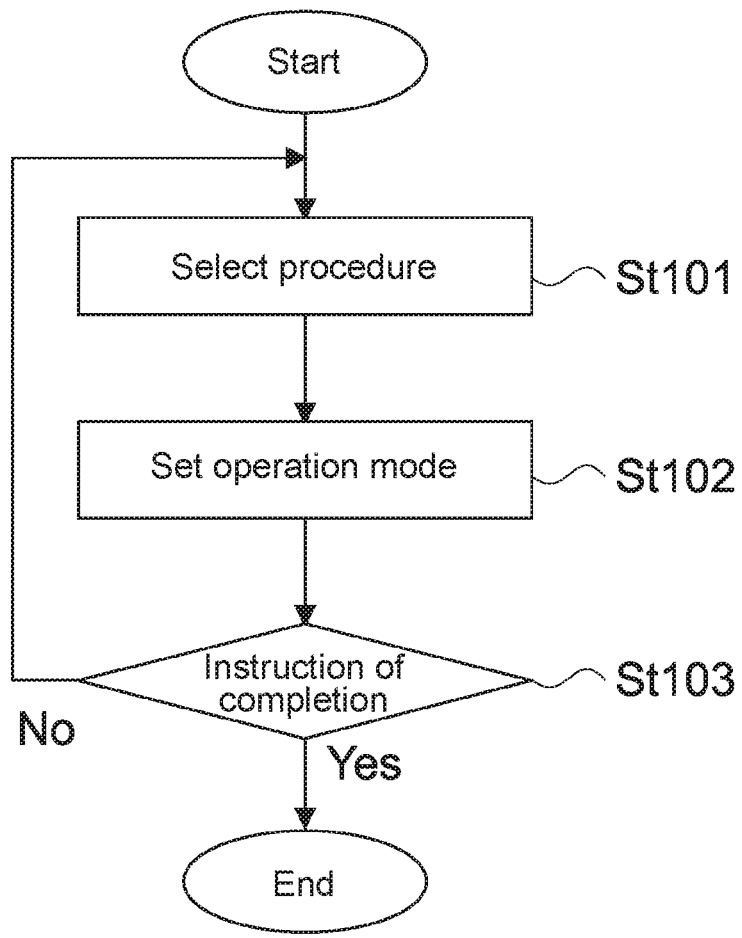
FIG. 6 is a flowchart illustrating an operation of the image processing system.

FIG. 6 is a flowchart illustrating an operation of the image processing system 100. As illustrated in the figure, the controller 104 selects a procedure (St101). The controller 104 can select a procedure according to a state recognition that is performed using image information regarding a front image.

Further, the controller 104 may select a procedure in response to an instruction given by a user, or may select a procedure according to both the instruction of the user and the state recognition. This will be described in detail later.

Next, the controller 104 sets an operation mode depending on a result of selecting a procedure (St102). With respect to the operation mode for each procedure (refer to FIG. 5), an operation state of each of the sections that is suitable to perform the procedure, is preset. The operation mode includes a method for acquiring cross-sectional information that is performed by the cross-sectional information acquisition section 1012, and a method for presenting cross-sectional information or a method for presenting a graphical user interface (GUI) that is performed by the display information generator 105.

For example, when the creating a wound (1-1) of the PEA is selected in a procedure selection step (St101), the controller 104 controls each section of the image processing system 100 such that an operation is performed in an operation mode set for the creating a wound. A specific operation of the image processing system 100 in an operation mode corresponding to each procedure will be described later.

The controller 104 completes the operation when the controller 104 receives an instruction of completion from the user (St103: Yes), and the controller 104 repeatedly performs the operation described above when the controller 104 does not receive the instruction of completion from the user (St103: No).

[Regarding Selection of Procedure]

The procedure selection step (St101) is described in detail. As described above, the controller 104 determines a procedure according to one of an instruction given by a user and a state recognition, or according to both of them.

The controller 104 can select a procedure in response to an instruction given by a user. The display information generator 105 can display, on the display section 106, a procedure in the form of a menu, and the user can designate a procedure through an input device such as a foot switch. The controller 104 can select the procedure designated by the user.

Further, the controller 104 may determine the instruction of the user using a result of a recognition performed by the image recognition section 102 with respect to a front image. The image recognition section 102 recognizes a surgical tool included in the front image, and provides a result of the recognition to the controller 104. The controller 104 can determine the procedure designated by the user using a position of the tip of the surgical tool in the front image, and can select the procedure.

Further, the controller 104 can select a procedure using a state recognition with respect to a front image. The state recognition is to recognize a state using the characteristics of a front image or a result of an image recognition performed by the image recognition section 102. Examples of the characteristics of a front image include a difference in brightness between a peripheral portion of the front image and a central portion of the front image, the brightness of the entire front image, and a distribution of color in the front image.

Furthermore, the controller 104 can also determine a state using a result of a recognition performed by the image recognition section 102 with respect to a front image or cross-sectional information. Specifically, the controller 104 can perform a state recognition using, for example, the type of surgical tool included in a front image, the distance between a surgical tool and a site of an eye, or the movement speed of the tip of a surgical tool.

Moreover, the controller 104 may perform a state recognition using both the characteristics of a front image and a result of an image recognition performed by the image recognition section 102. Specifically, the controller 104 can recognize a surgical technique from the characteristics of a front image, and can specify a procedure included in the surgical technique using a result of a recognition performed by the image recognition section 102. For example, if the controller 104 recognizes vitreoretinal surgery from the fact that a peripheral portion of a front image is dark (a state in which a certain portion inside an eye is illuminated using a light guide) and recognizes that there exists a pair of tweezers for inner limiting membrane in the front image, the controller 104 can select a procedure of membrane processing in vitreoretinal surgery.

A specific example of the controller 104 selecting a procedure, is described below.

(Procedure Selection Performed According to Instruction of User)

Figure 7:
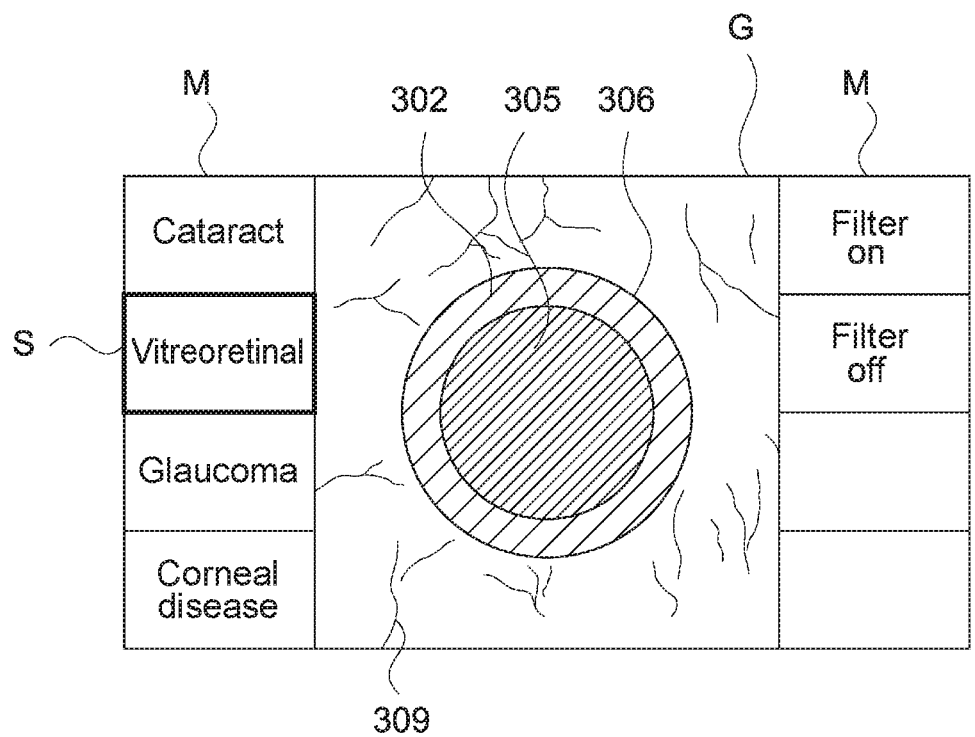
FIG. 7 is a schematic diagram illustrating a method for designating a procedure in the image processing system.
Figure 8:
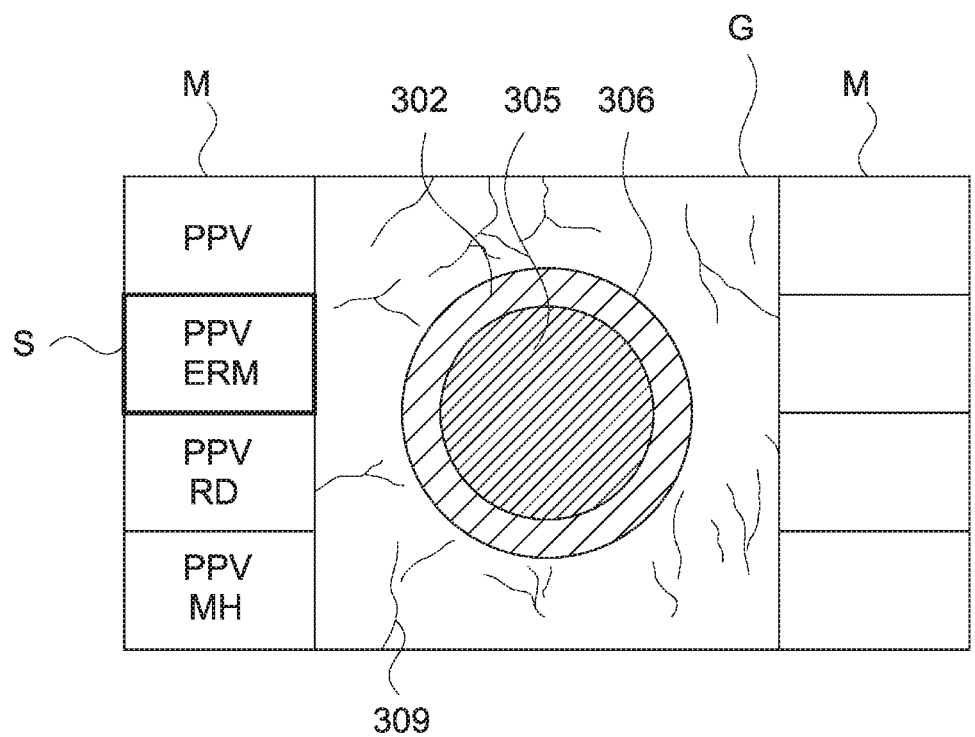
FIG. 8 is a schematic diagram illustrating the method for designating a procedure in the image processing system.
Figure 9:
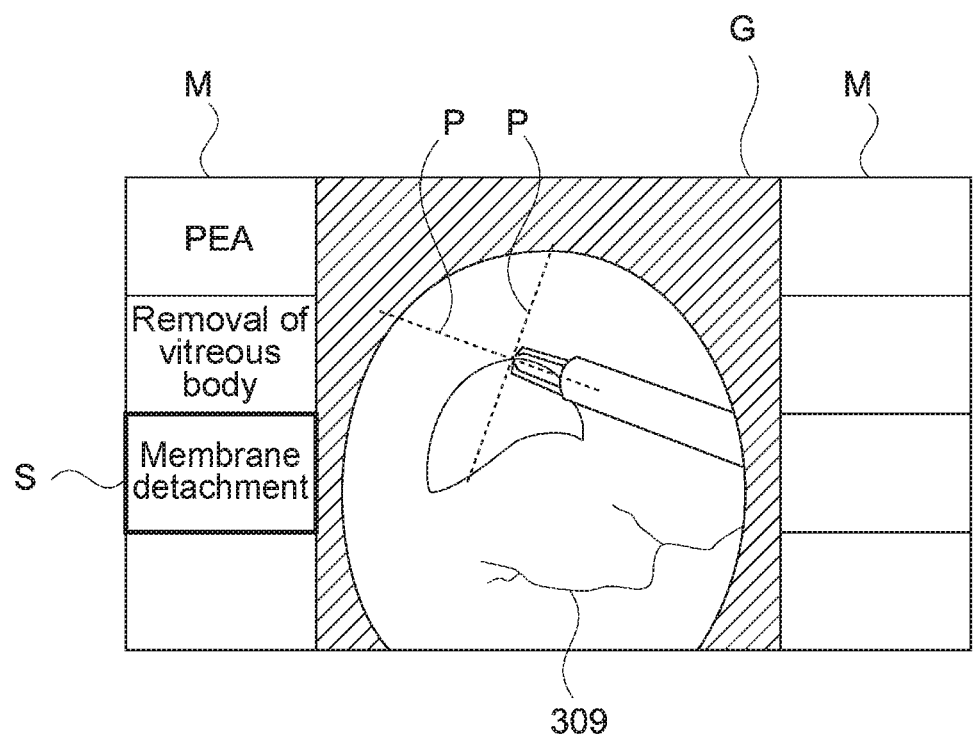
FIG. 9 is a schematic diagram illustrating the method for designating a procedure in the image processing system.

FIGS. 7 to 9 are schematic diagrams illustrating a procedure selection performed according to an instruction of a user, and are an example of selecting a procedure of membrane detachment in vitrectomy (PPV) with respect to epi-retinal membrane (ERM), which is a kind of vitreoretinal surgery.

In accordance with a control performed by the controller 104, the display information generator 105 generates display information illustrated in FIGS. 7 to 9, and displays the display information on the display section 106. As illustrated in FIGS. 7 to 9, the display information includes a front image G captured by the front image acquisition section 1011, and a menu (M in the figures).

A user can select an item from the menu M using an input device such as a foot switch. In FIGS. 7 to 9, a selected item is indicated using a box S. As illustrated in the figure, first, the user selects "vitreoretinal" as a type of disease. Then, as illustrated in FIG. 8, the controller 104 displays a surgical technique included in "vitreoretinal" on the menu M.

Next, the user selects, from the menu M, the surgical technique of vitrectomy with respect to epi-retinal membrane ("PPV ERM" in the figure). As illustrated in FIG. 9, the controller 104 displays procedures included in the PPV ERM (refer to FIG. 5) as the menu M.

Next, the user selects membrane detachment from the menu M using the input device such as a foot switch. This causes the controller 104 to select the procedure "membrane detachment" and to set an operation mode for membrane detachment. FIG. 9 illustrates a cross-sectional position P in an operation mode suitable for membrane detachment.

(Procedure Selection Performed According to Instruction of User and State Recognition)

Figure 10:
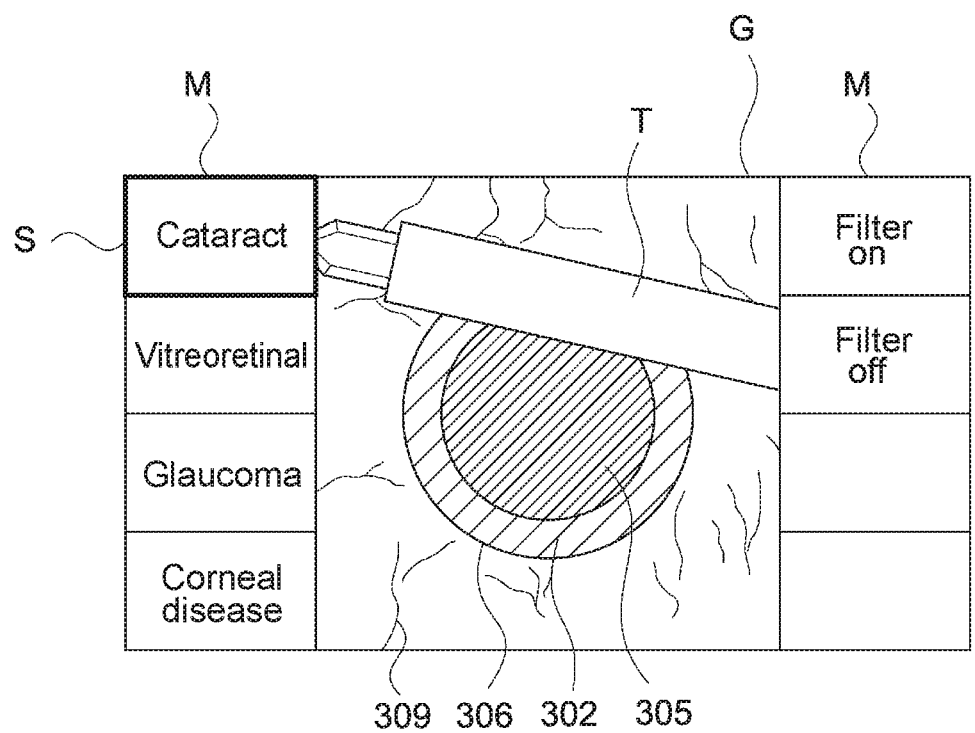
FIG. 10 is a schematic diagram illustrating a method for designating a procedure in the image processing system.
Figure 11:
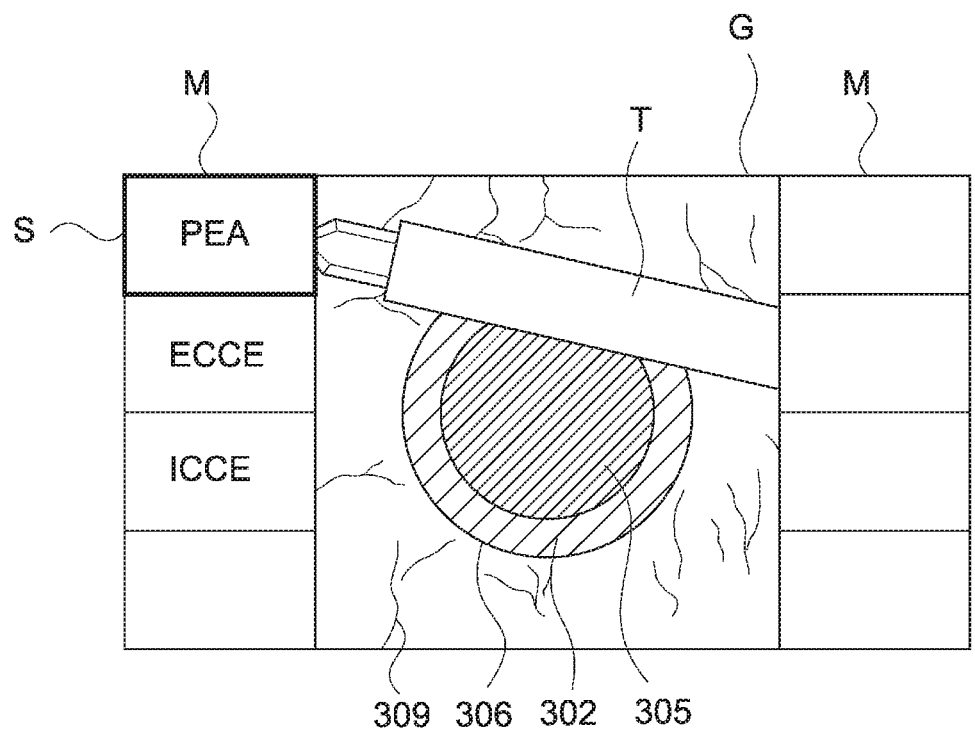
FIG. 11 is a schematic diagram illustrating the method for designating a procedure in the image processing system.
Figure 12:
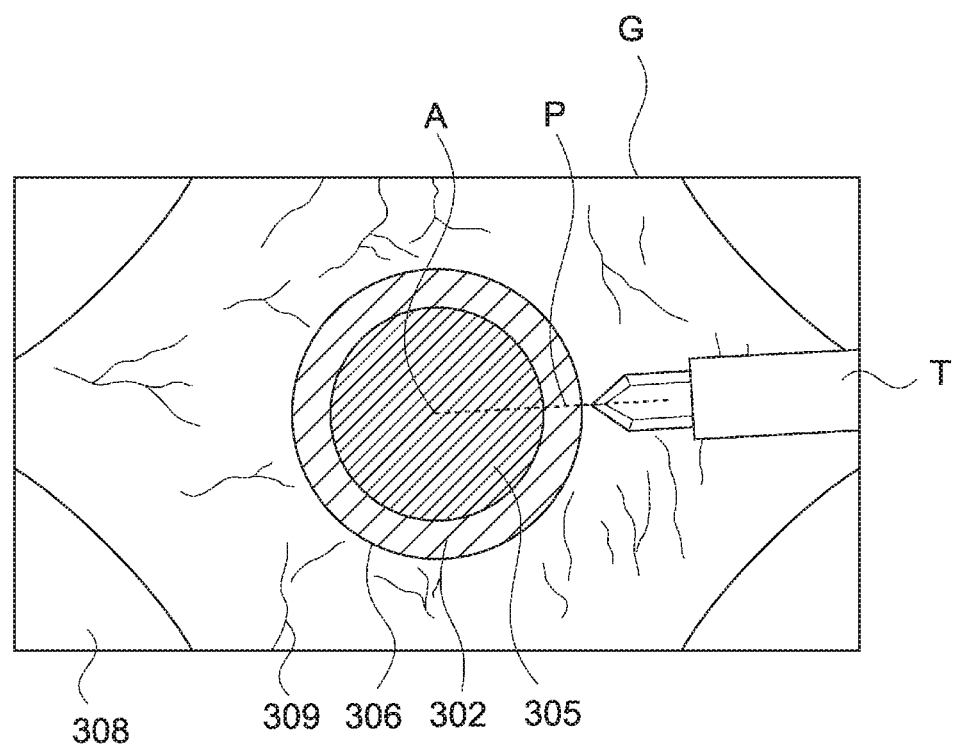
FIG. 12 is a schematic diagram illustrating the method for designating a procedure in the image processing system.

FIGS. 10 to 12 are schematic diagrams illustrating a procedure selection performed according to an instruction of a user and a state recognition, and are an example of selecting a procedure of creating a wound in phacoemulsification and aspiration (PEA), which is a kind of cataract surgery.

In accordance with a control performed by the controller 104, the display information generator 105 generates display information illustrated in FIGS. 10 to 12, and displays the display information on the display section 106. As illustrated in FIGS. 10 to 12, the display information includes a front image G (G in the figures) captured by the front image acquisition section 1011, and a menu (M in the figures, except for FIG. 12).

As illustrated in FIG. 10, a user can select an item (indicated using a box S in the figures) from the menu M. Here, the user can select an item using a position of the tip of a surgical tool T. As illustrated in FIG. 10, the user moves the position of the tip of the surgical tool T into a box of an item that the user wishes to select ("cataract" in the figure). The controller 104 can grasp a positional relationship between the tip of surgical tool T and the menu M by the image recognition section 102 performing an object recognition with respect to the surgical tool T.

The user can select an item by a method such as moving the tip of the surgical tool T into a box of a specific item, and giving a determination instruction using a foot switch or keeping the tip of the surgical tool T in the box of the specific item for a certain period of time or more.

When the user selects "cataract" as a type of disease, as illustrated in FIG. 10, the controller 104 displays a surgical technique included in cataract as the menu M, as illustrated in FIG. 11. Next, the user selects the surgical technique of PEA from the menu M. As describe above, the user can select an item of the menu M using the position of the tip of the surgical tool T.

When the PEA is selected, the controller 104 acquires a result of an image recognition performed by the image recognition section 102. The controller 104 compares a surgical tool that is likely to be used for PEA with the result of the image recognition, and specifies a recognized surgical tool. The controller 104 selects a procedure in which the specified surgical tool is used. The controller 104 selects creation of a wound as a procedure because the surgical tool T used for creation of a wound is recognized as illustrated in FIG. 12, and sets an operation mode for creation of a wound.

(Procedure Selection Performed According to State Recognition)

Figure 13:
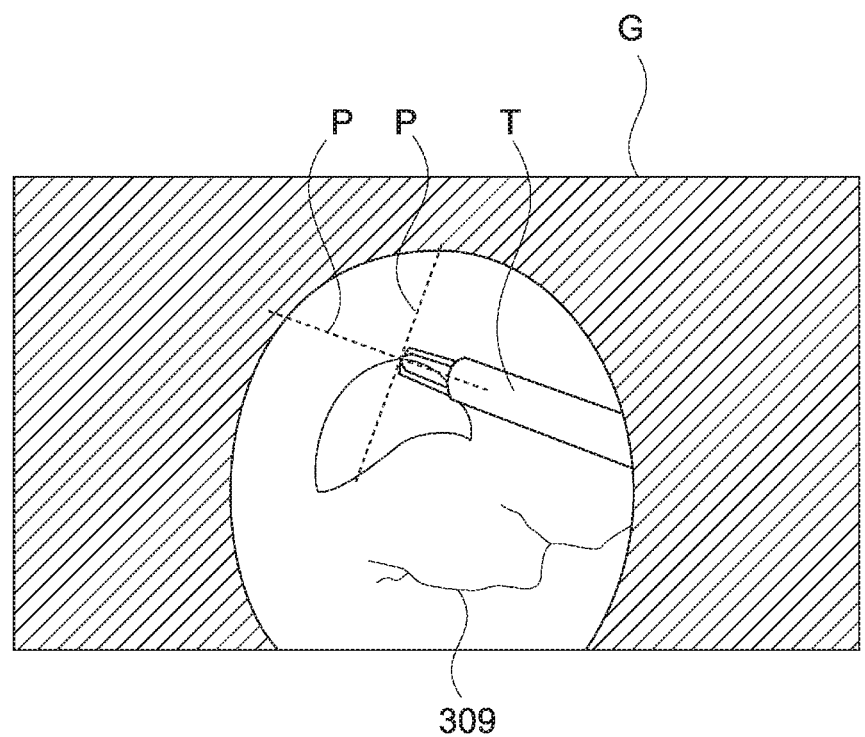
FIG. 13 is a schematic diagram illustrating cross-sectional positions set by the image processing system.

FIG. 13 is a schematic diagram illustrating a procedure selection performed according to a state recognition, and is an example of selecting a procedure of membrane detachment in vitrectomy (PPV) with respect to epi-retinal membrane (ERM), which is a kind of vitreoretinal surgery.

The controller 104 selects a procedure using the characteristics of a front image G and a result of an image recognition performed by the image recognition section 102. Specifically, from the fact that a peripheral portion of the front image G is dark (the shaded region in the figure), the controller 104 can determine that the surgery that is being carried out is vitreoretinal surgery. Further, the controller 104 uses a result of a recognition of a surgical tool and of a site of an eyeball that is performed by the image recognition section 102, and, from the fact that the surgical tool T is a pair of tweezers for inner limiting membrane, the tip of the surgical tool T is situated close to a retina, the tip of the surgical tool T is situated close to a macular region, and the movement of the tip of the surgical tool T is slow, the controller 104 can presume that a procedure that is being performed under surgery of membrane detachment is membrane detachment. Accordingly, the controller 104 selects the procedure of "membrane detachment" and sets an operation mode for membrane detachment.

As described above, the controller 104 can select a procedure according to one of an instruction given by a user and a state recognition, or according to both of them. Note that how to perform selection may be selected by a manufacturer in advance to be provided, or it is also possible to prepare a plurality of options and to select one of the plurality of options in advance according to what an operator wishes.

Further, the controller 104 may separately select respective procedures included in each surgical technique (refer to FIG. 5) using the methods described above, and after selecting a specific procedure using the method described above, the controller 104 may select a procedure as the surgical technique proceeds. For example, when creation of a wound is completed in PEA and then an operator inputs an instruction indicating the matter, the controller 104 can select incision of an anterior capsule, which is a procedure subsequent to the creation of a wound.

[Regarding Operation Mode]

The operation-mode setting step (St102) is described in detail. As described above, when the controller 104 selects a procedure, the controller 104 controls one of the cross-sectional information acquisition section 1012 and the display information generator 105 or both of them, such that an operation is performed in an operation mode suitable to perform the selected procedure.

The operation mode corresponding to each procedure includes a method for acquiring cross-sectional information, a method for presenting cross-sectional information, and a method for presenting a GUI.

In the method for acquiring cross-sectional information, according to a shape of a surgical tool recognized in a front image by the image recognition section 102, the controller 104 can determine a position of a cross section for which cross-sectional information is to be acquired. For example, the controller 104 can set a plane in parallel with the longitudinal direction of a surgical tool to be the cross section, or can set, to be the cross section, a plane that intersects the longitudinal direction of the surgical tool at a certain angle (refer to FIG. 13).

Further, according to a site of an eye that is recognized by the image recognition section 102 in a front image, the controller 104 can determine a position of a cross section for which cross-sectional information is to be acquired. For example, the controller 104 can set, to be the cross section, a plane passing through a site that is gazed at in a specific procedure (refer to FIG. 16) or a plane centered on a specific site (refer to FIG. 14).

Furthermore, according to a surgical tool and a site of an eye that are recognized by the image recognition section 102 in a front image, the controller 104 can determine a position of a cross section for which cross-sectional information is to be acquired. For example, the controller 104 can set, to be the cross section, a plane passing through the surgical tool and a specific site of the eye (refer to FIG. 12).

The controller 104 can also fix a position of a cross section in response to an instruction input performed by a user or can release the fixation. Moreover, the controller 104 may perform a fine adjustment of the position of the cross section in response to the instruction input performed by the user or may cause the cross section to follow a surgical tool or a site of an eye.

The controller 104 determines, according to a selected procedure, by which method cross-sectional information is to be acquired, and controls the cross-sectional information acquisition section 1012 to acquire the cross-sectional information using the determined acquisition method. The cross-sectional information is not limited to a cross-sectional image, and may be volume data generated from cross-sectional images successively captured by shifting a cross section, or may be a moving image constituted of cross-sectional images. The method for acquiring cross-sectional information corresponding to each procedure will be described later.

In the method for presenting cross-sectional information, the controller 104 can control the display information generator 105 to change a position of cross-sectional information according to a position of a cross section when the display information generator 105 generates display information including the cross-sectional information (refer to FIG. 39). Further, the controller 104 can control the display information generator 105 to change an orientation of cross-sectional information according to an orientation of a cross section (refer to FIG. 38).

Figure 18:
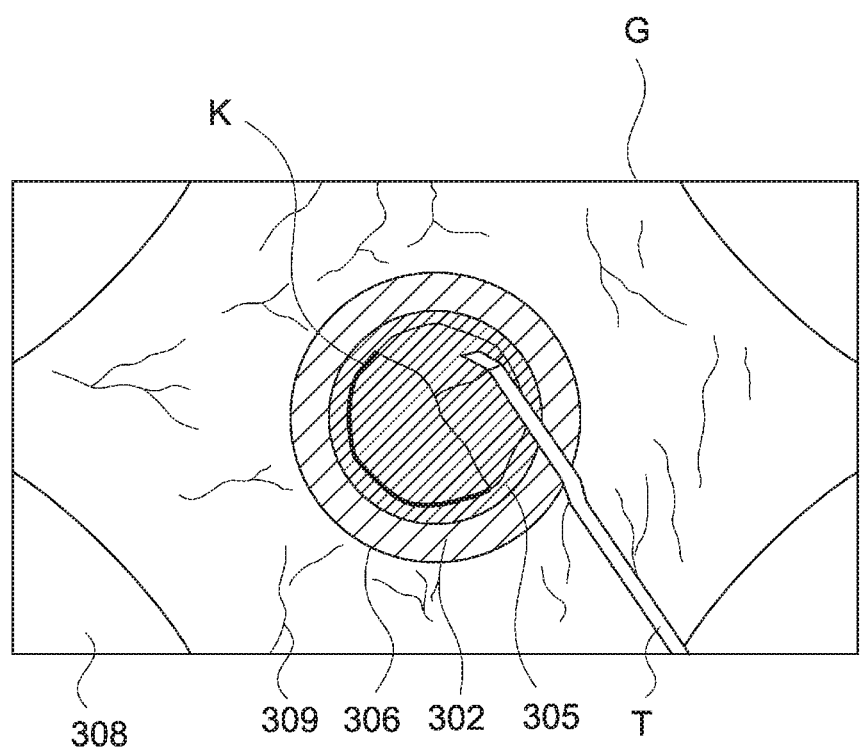
FIG. 18 is a schematic diagram illustrating an incision edge detected by the image processing system.

Moreover, the controller 104 can detect an incision edge formed by performing treatment, using a result of a recognition performed by the image recognition section 102 with respect to cross-sectional information, and can control the display information generator 105 to generate display information by superimposing an image including the incision edge on a front image (refer to FIG. 18).

From a result of a recognition performed by the image recognition section 102 with respect to a front image, the controller 104 can determine a position of a cross section according to a position of a surgical tool included in the front image, and can control the display information generator 105 to generate display information including cross-sectional information that varies according to the cross-sectional position (refer to FIG. 39).

Figure 42:
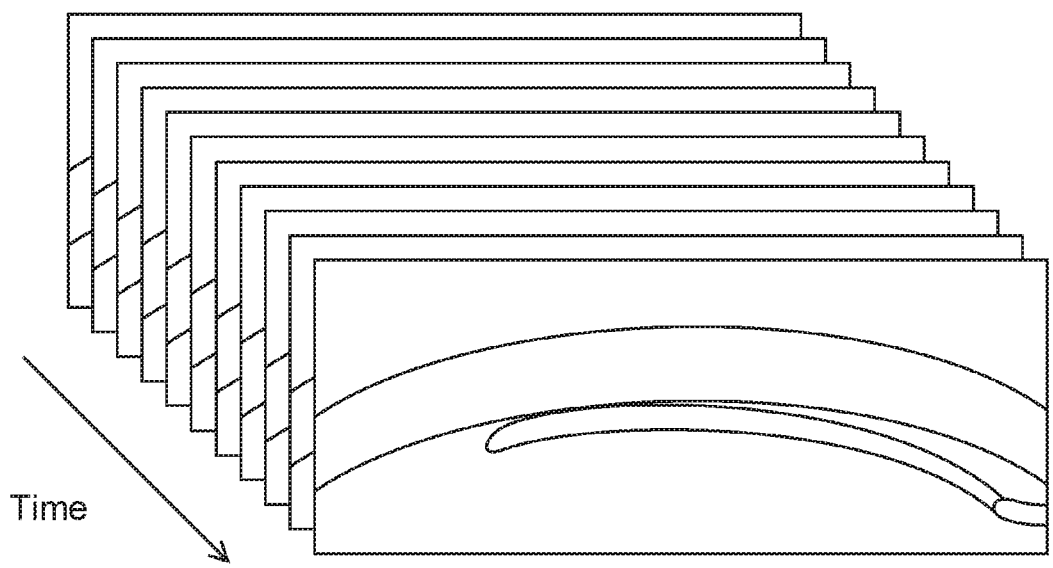
FIG. 42 schematically illustrates a moving image that is constituted of cross-sectional images and acquired by the image processing system.

The controller 104 can control the cross-sectional information acquisition section 1012 to acquire a moving image obtained by recording cross-sectional images for a certain period of time, and can control the display information generator 105 to present the moving image (refer to FIG. 42).

The controller 104 can control the cross-sectional information acquisition section 1012 to acquire cross-sectional images for a certain period of time according to a position of a surgical tool recognized by the image recognition section 102, and can generate volume data from a group of the cross-sectional images. The controller 104 can control the display information generator 105 to present the volume data (refer to FIG. 43). The method for presenting cross-sectional information corresponding to each procedure will be described later.

Figure 33:
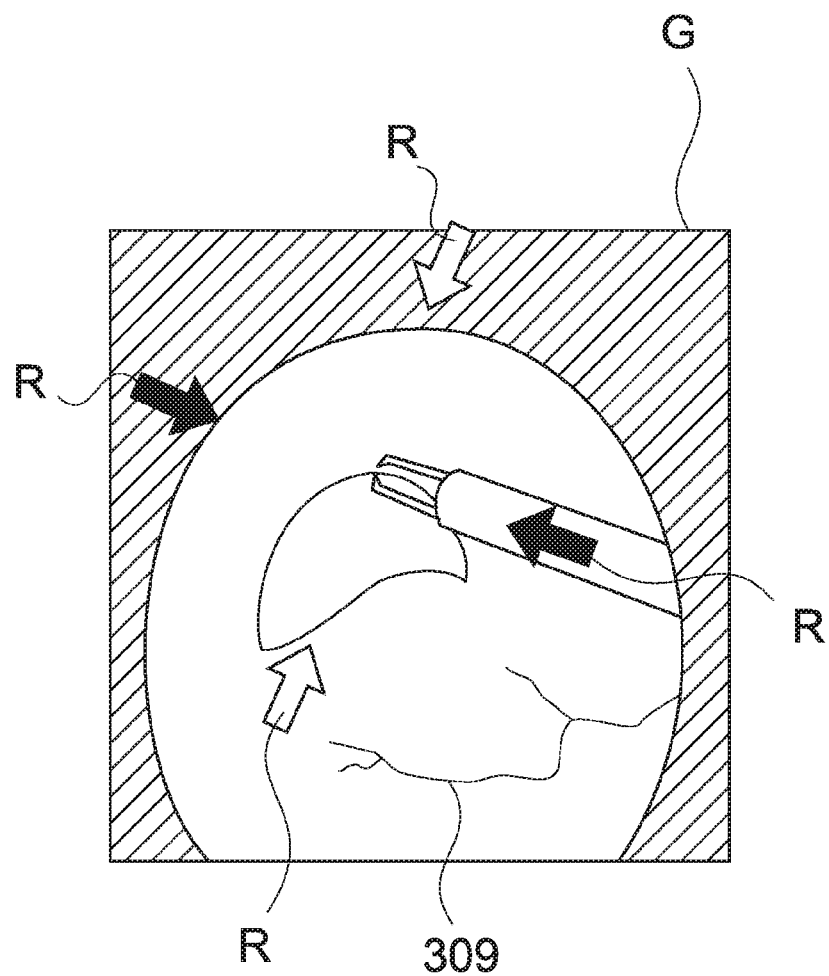
FIG. 33 schematically illustrates an image indicating a cross-sectional position presented by the image processing system.

In the method for presenting a GUI, the controller 104 can control the display information generator 105 to generate display information by superimposing, on a front image, an image indicating an end point of a cross-sectional line indicating a position of a cross section (refer to FIG. 33). Further, the controller 104 can control the display information generator 105 to generate display information by processing a front image to depict a cross-sectional line indicating a position of a cross section (refer to FIG. 34).

The performing the processing to depict a cross-sectional line may be processing an image region corresponding to a cross-sectional line, or may be processing an image region other than the image region corresponding to the cross-sectional line. The controller 104 can perform the processing to depict a cross-sectional line by causing the display information generator 105 to change at least one of the level of a saturation of color or the level of brightness in a region to be processed.

Figure 35:
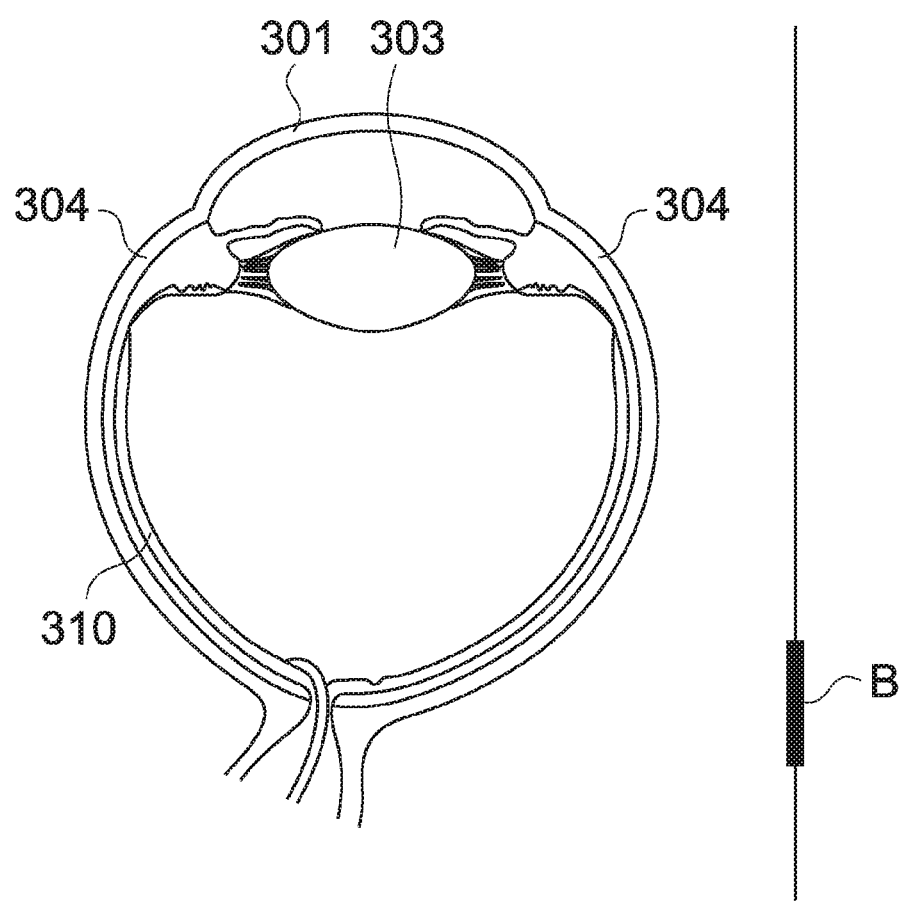
FIG. 35 schematically illustrates an image indicating the depth of a cross-sectional position presented by the image processing system.
Figure 36:
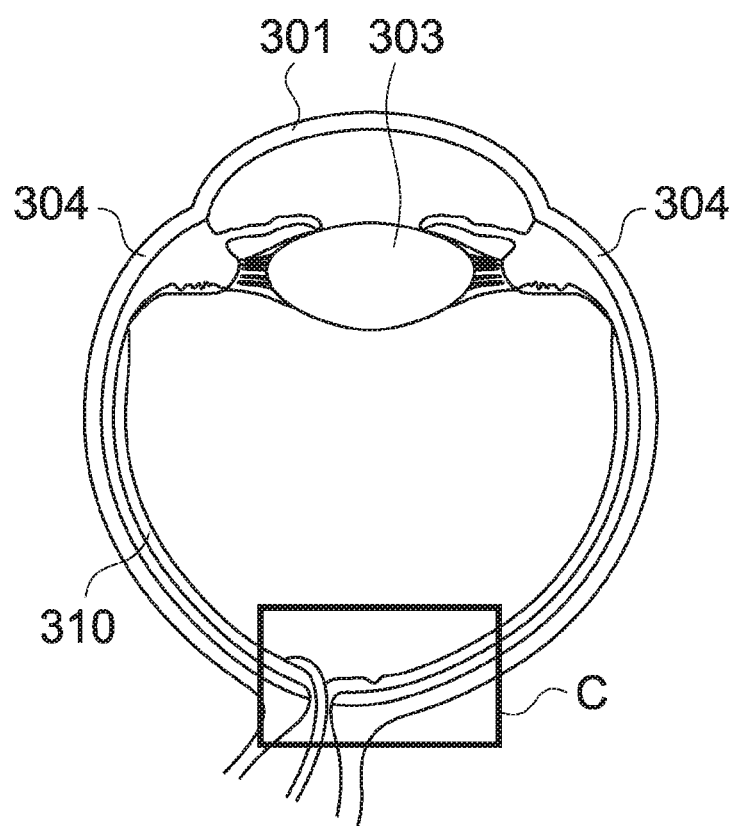
FIG. 36 schematically illustrates an image indicating the depth of a cross-sectional position presented by the image processing system.

Further, the controller 104 can control the display information generator 105 to generate display information including cross-sectional information and a position of a cross section in a depth direction with respect to the schematic diagram of an eye (refer to FIGS. 35 and 36). The method for presenting a GUI corresponding to each procedure will be described later.

[Regarding Operation Mode Depending on Procedure]

In the image processing system 100, the controller 104 selects a procedure and sets an operation mode depending on the procedure, as described above. The operation mode depending on each procedure is described below.

<Regarding Method for Acquiring Cross Section>

[Surgical Technique: Cataract PEA]

(Creation of Wound)

In creation of a wound, incision is performed in a direction of the center of the cornea 301 (refer to FIG. 4) from an extraocular region. Thus, as illustrated in FIG. 12, the controller 104 sets, to be a cross-sectional position P in a front image, a plane formed by connecting the tip of the surgical tool T to a cornea's center (A in the figure), where the length of the plane is slightly extended at both ends. The cross-sectional position P in a depth direction is set such that it is centered at, for example, a height of the iridocorneal angle 307. The controller 104 controls the cross-sectional information acquisition section 1012 to acquire a cross-sectional image of this cross-sectional position P. Accordingly, referring to the cross-sectional image, it is possible to easily grasp, for example, whether an angle of insertion of a surgical tool is appropriate and whether a wound is completely formed.

(Incision of Anterior Capsule 1)

Figure 14:
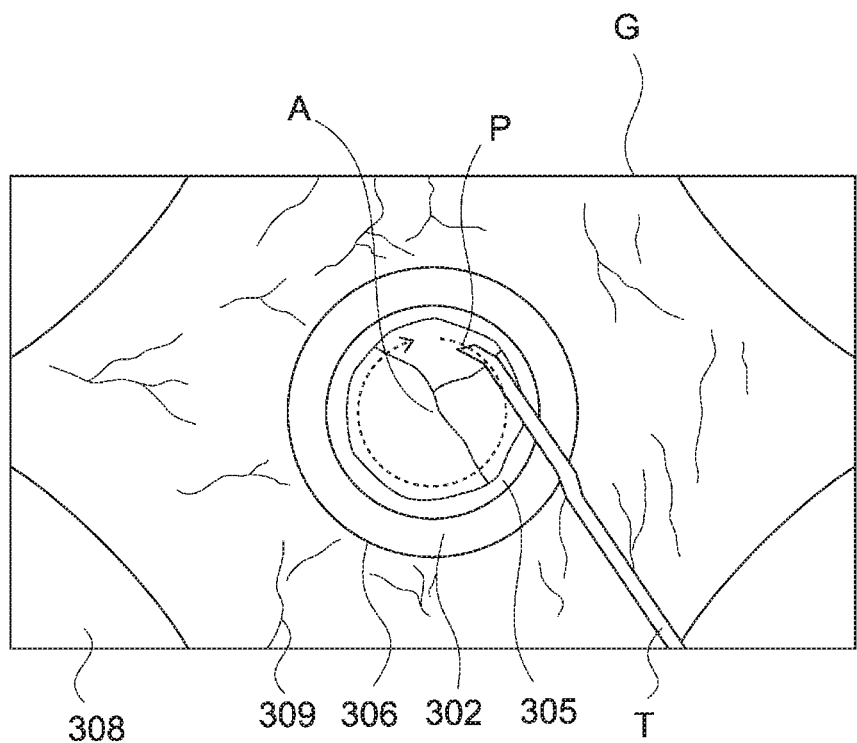
FIG. 14 is a schematic diagram illustrating a cross-sectional position set by the image processing system.
Figure 15:
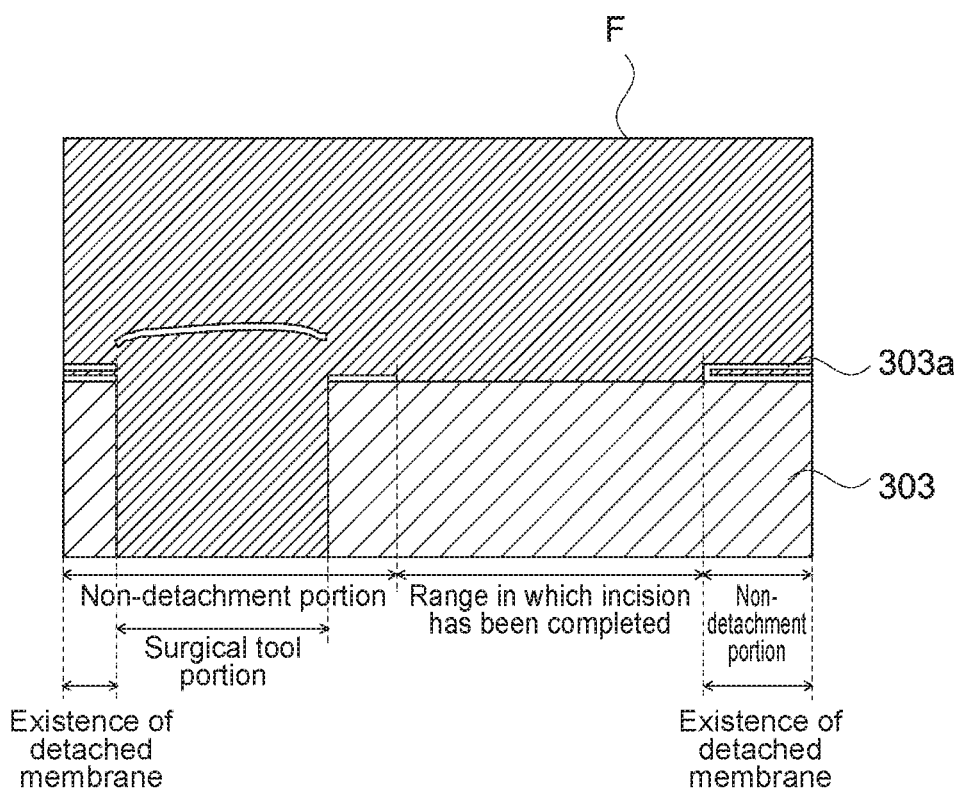
FIG. 15 illustrates an example of cross-sectional information acquired at the cross-sectional position set by the image processing system.

FIG. 14 is a schematic diagram illustrating a cross-sectional position P in a front image G when an anterior capsule is incised. The anterior capsule 303a is less visible in the incision of an anterior capsule, and thus it is not easy to know to what extent the incision has progressed. Thus, as illustrated in FIG. 14, the controller 104 controls the cross-sectional information acquisition section 1012 to scan a circle that is a cross-sectional position P from a start point to an end point of the arrow, the circle being centered on the cornea's center A and having a diameter of about 3 to 4 mm. The cross-sectional position P in a depth direction is set such that it is centered at, for example, a height of the anterior capsule 303a. FIG. 15 illustrates a cross-sectional image acquired with respect to the cross-sectional position P. As can be seen from the figure, it becomes easy to know a range in which the incision has been completed (a range in which the anterior capsule 303a has been detached).

(Incision of Anterior Capsule 2)

Figure 16:
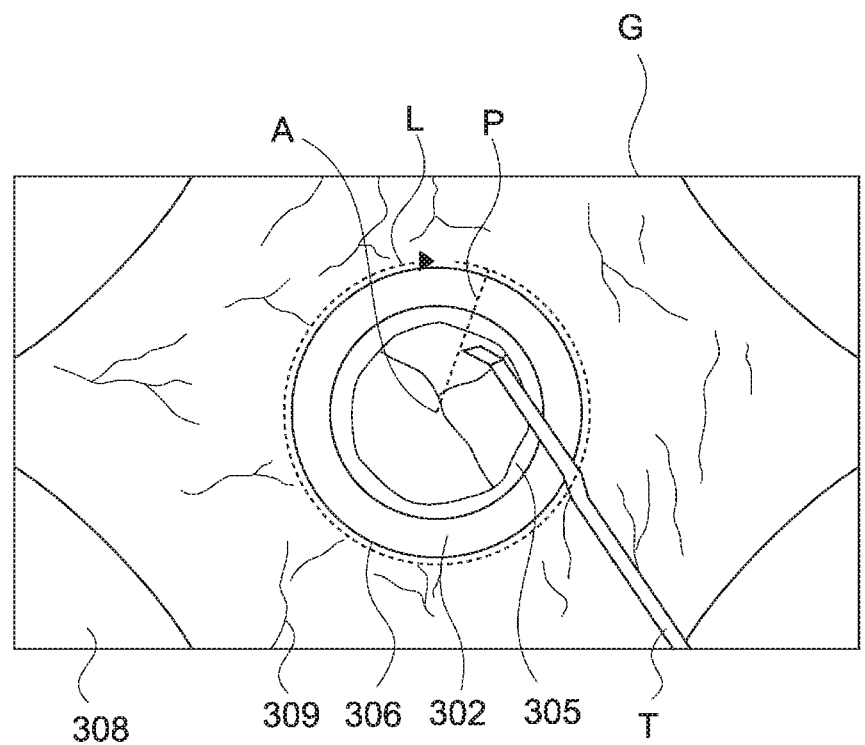
FIG. 16 is a schematic diagram illustrating a cross-sectional position set by the image processing system.

FIG. 16 is a schematic diagram illustrating a cross-sectional position P in the front image G when an anterior capsule is incised. Since the anterior capsule 303a is less visible in the incision of an anterior capsule, there may be a need to confirm not only a range in which the incision has been completed, but also a distance of an incision edge from a cornea's center. Thus, as illustrated in FIG. 16, the controller 104 sets, to be the cross-sectional position P, a plane formed by connecting the cornea's center A to the corneal limbus 306, and periodically rotates this line about the cornea's center A, as indicated by an arrow L. The cross-sectional position P in a depth direction is set such that it is centered at, for example, a height of the anterior capsule 303a. The controller 104 controls the cross-sectional information acquisition section 1012 to acquire a cross-sectional image of the rotated cross-sectional position P at each angle.

Figure 17:
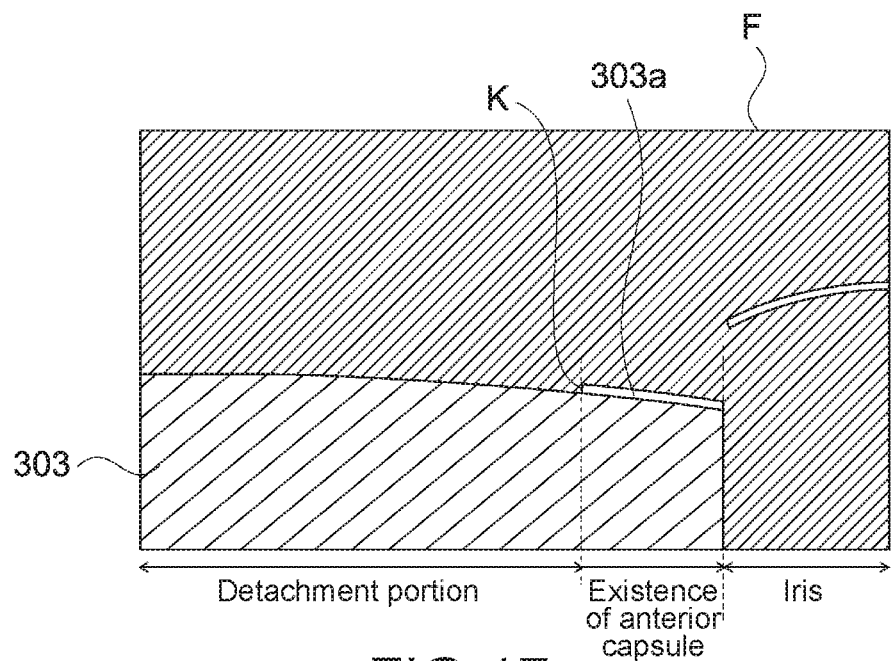
FIG. 17 illustrates an example of cross-sectional information acquired at a cross-sectional position set by the image processing system.

FIG. 17 illustrates a cross-sectional image F acquired with respect to a cross-sectional position P (a rotated cross-sectional position P at one of the angles). As can be seen from the figure, it becomes easy to know an incision edge (K in the figure) of the anterior capsule 303a. Further, from a result of a recognition performed by the image recognition section 102, the controller 104 can also detect incision edges in the cross-sectional images F captured at respective angles, and can combine the incision edges. The controller 104 may control the display information generator 105 to superimpose the combined incision edges on the front image G. FIG. 18 illustrates a front image G on which the combined incision edges K captured at the respective angles are superimposed.

Note that the controller 104 may set a plane in parallel with the longitudinal direction of the tip of a surgical tool to be the cross-sectional position P, without rotating the cross-sectional position P as illustrated in FIG. 16.

(Formation of Incision)

Figure 19:
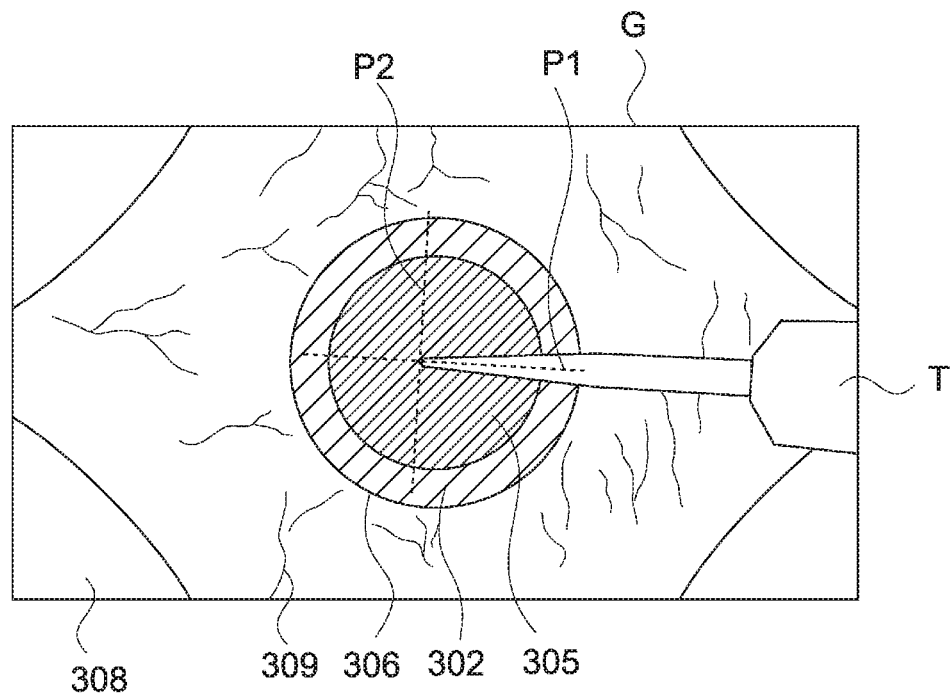
FIG. 19 is a schematic diagram illustrating cross-sectional positions set by the image processing system.

FIG. 19 is a schematic diagram illustrating cross-sectional positions P1 and P2 in a front image G when an incision is formed. In the formation of an incision, a surgical tool is moved forward from the front side in parallel with the longitudinal direction of a surgical tool, so as to proceed with incising a nucleus of the crystalline lens 303. Here, due to lack of depth information, a surgical tool may erroneously reach the posterior capsule 303b (refer to FIG. 4) and damage the posterior capsule 303b. Thus, as illustrated in FIG. 19, the controller 104 sets, to be the cross-sectional position P1, a plane passing through the tip of the surgical tool T and extending in parallel with the longitudinal direction of the surgical tool T.

Further, as illustrated in the figure, the controller 104 may set, to be the cross-sectional position P2, a plane passing through the tip of the surgical tool T and extending orthogonally to the longitudinal direction of the surgical tool T. It is favorable that ranges of the cross-sectional positions P1 and P2 each be roughly from one side of the corneal limbus 306 to the other side of the corneal limbus 306. The cross-sectional positions P1 and P2 in a depth direction are each set such that, for example, the level of the top of the posterior capsule 303b (in FIG. 4, a downmost point in the downwardly convex portion of the crystalline lens 303) is situated slightly higher than the lower end of the cross section.

The controller 104 controls the cross-sectional information acquisition section 1012 to acquire cross-sectional images of these cross-sectional positions P1 and P2. Accordingly, it becomes easy to understand a positional relationship between the surgical tool T and the posterior capsule 303b, which results in being able to prevent the posterior capsule 303b from being damaged.

(Division of Nucleus)

Figure 20:
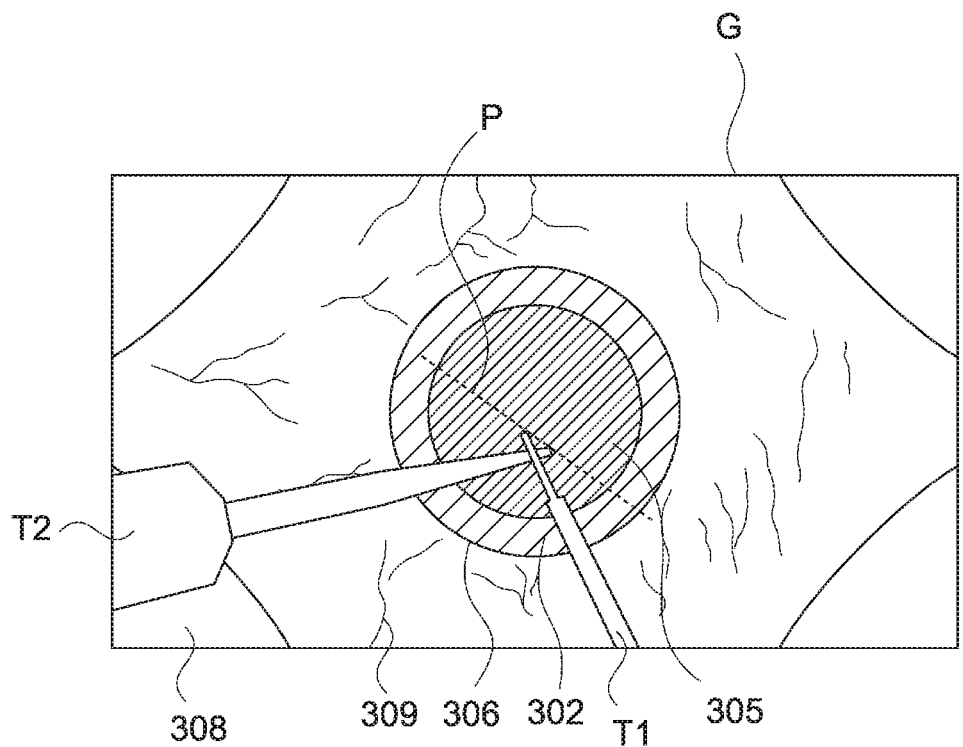
FIG. 20 is a schematic diagram illustrating a cross-sectional position set by the image processing system.

FIG. 20 is a schematic diagram illustrating a cross-sectional position P in a front image G when a nucleus is divided. In the division of a nucleus, it is important that both a phacoemulsification tip (a phaco tip) and a hook be at a sufficiently deep position, but there is a possibility that the division will fail due to the division accidentally being performed when they are at a shallow position. Thus, as illustrated in FIG. 20, the controller 104 sets, to be the cross-sectional position P, a plane passing through both of the tips of a phaco tip T2 and a hook T1. The cross-sectional position P in a depth direction is set such that, for example, an average of the depth positions of both of the surgical tools is the center of the cross section.

The controller 104 controls the cross-sectional information acquisition section 1012 to acquire a cross-sectional image of this cross-sectional position P. Accordingly, it becomes easy to understand, in a cross-sectional image, the depths of a phaco tip and a hook in a crystalline lens.

(Aspiration of Nucleus)

It is important to grasp a positional relationship between the tip of a surgical tool and the crystalline lens 303 when a nucleus is aspirated. Thus, as illustrated in FIG. 19, the controller 104 sets, to be the cross-sectional position P1, a plane passing through the tip of the surgical tool T and extending in parallel with the longitudinal direction of the surgical tool T, and the controller 104 sets, to be the cross-sectional position P2, a plane passing through the tip of the surgical tool T and intersecting the longitudinal direction of the surgical tool T at a certain angle (for example, 90 degrees). The cross-sectional positions P1 and P2 in a depth direction are set such that they are centered at, for example, a depth of the position of the tip of the surgical tool. Further, the level of the top of the posterior capsule 303b (in FIG. 4, a downmost point in a downwardly convex portion of the crystalline lens 303) may be situated slightly higher than the lower end of the cross section.

The controller 104 controls the cross-sectional information acquisition section 1012 to acquire a cross-sectional image of this cross-sectional position P. This makes it possible to easily grasp a positional relationship between the tip of a surgical tool and the crystalline lens 303 in a cross-sectional image.

[Surgical Technique: Vitreoretinal Surgery]

(Removal of Vitreous Body)

Figure 21:
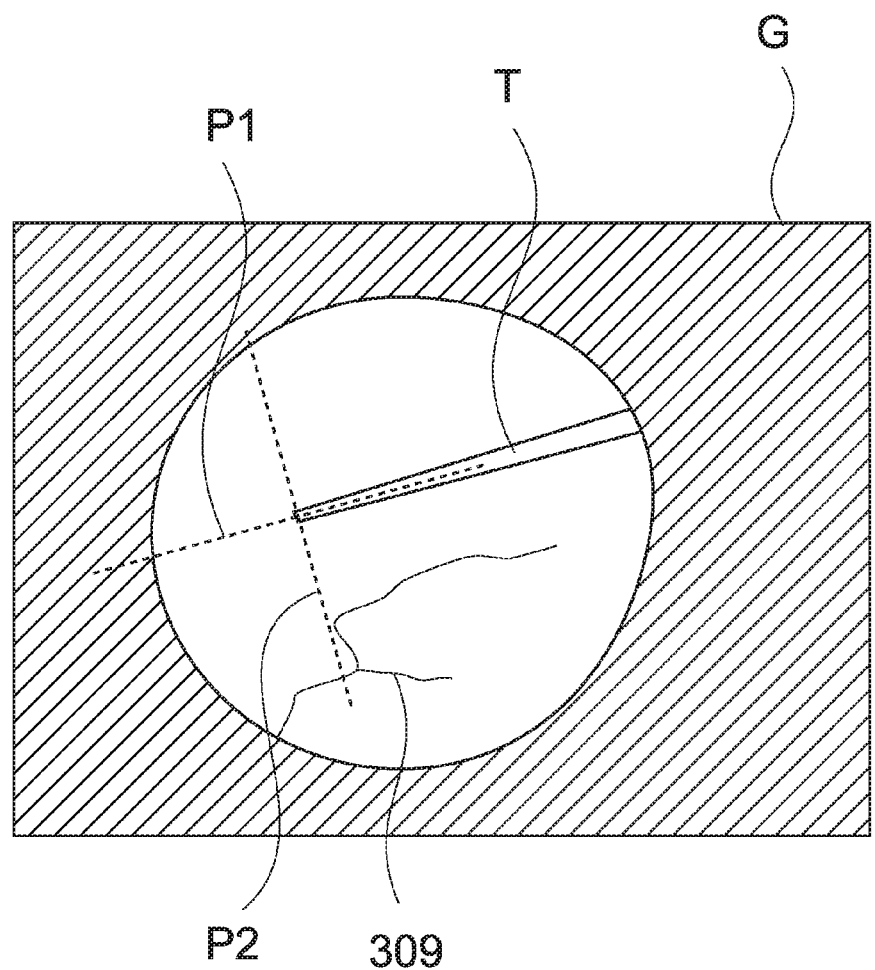
FIG. 21 is a schematic diagram illustrating cross-sectional positions set by the image processing system.

FIG. 21 is a schematic diagram illustrating cross-sectional positions P1 and P2 in a front image G when a vitreous body is removed. In the removal of a vitreous body, the tip of a surgical tool moves in a relatively wide range. Thus, as illustrated in FIG. 21, the controller 104 sets, to be the cross-sectional position P1, a plane passing through the tip of the surgical tool T and extending in parallel with the longitudinal direction of the surgical tool T, and the controller 104 sets, to be the cross-sectional position P2, a plane passing through the tip of the surgical tool T and intersecting the longitudinal direction of the surgical tool T at a certain angle (for example, 90 degrees). The cross-sectional positions P1 and P2 in a depth direction are set such that they are centered at, for example, a depth of the position of the tip of the surgical tool.

Figure 22:
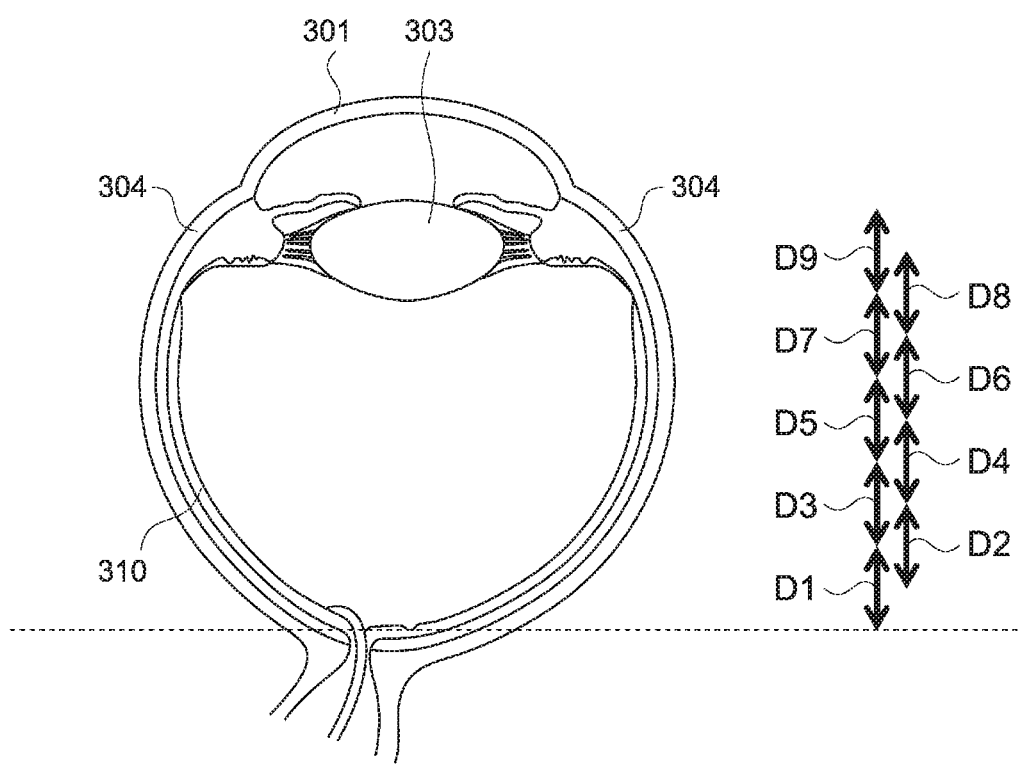
FIG. 22 is a schematic diagram illustrating a depth range of a cross-sectional position set by the image processing system.

Here, the controller 104 can also control the movement of a cross-sectional position in a depth direction using a different method. FIG. 22 is a schematic diagram illustrating a cross-sectional position in a depth direction. As illustrated in the figure, a plurality of depth ranges (D1 to D9) is defined, with the depth of a retina 310 being used as a reference. The controller 104 compares the depth of the center of each depth range with the depth of the tip of a surgical tool, and sets, to be the cross-sectional position, a depth range with a center whose depth is closest to the depth of the tip of the surgical tool.

The controller 104 controls the cross-sectional information acquisition section 1012 to acquire a cross-sectional image of this cross-sectional position. This results in the depth of a cross-sectional position not being changed even if the depth of the tip of a surgical tool is slightly changed, and this makes it possible to easily understand a positional relationship between the tip of a surgical tool and a retina in a cross-sectional image.

(Membrane Processing 1)

Figure 23:
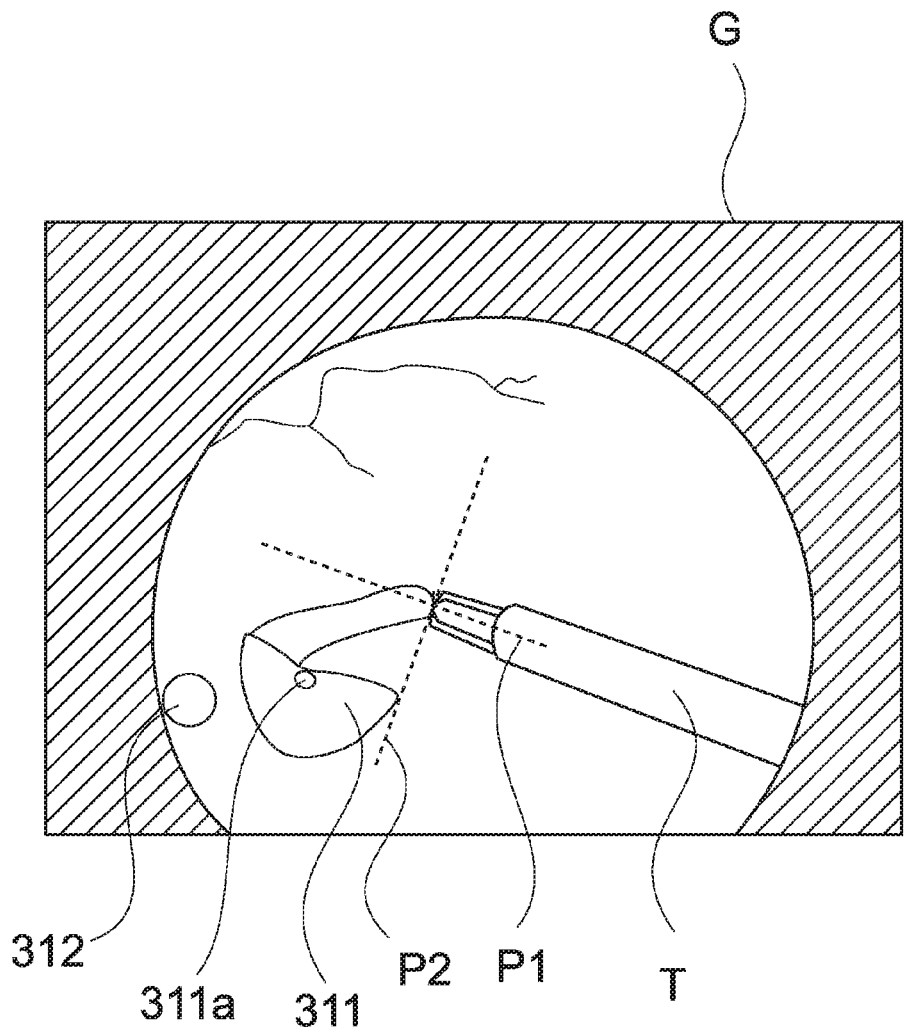
FIG. 23 is a schematic diagram illustrating cross-sectional positions set by the image processing system.

FIG. 23 is a schematic diagram illustrating cross-sectional positions P1 and P2 in a front image G1 when membrane processing is performed. In the membrane processing, there may be a need to grasp a depth relationship between the tip of a surgical tool and a retina. Thus, as illustrated in FIG. 23, the controller 104 sets, to be the cross-sectional position P1, a plane passing through the tip of the surgical tool T and extending in parallel with the longitudinal direction of the surgical tool T, and the controller 104 sets, to be the cross-sectional position P2, a plane passing through the tip of the surgical tool T and intersecting the longitudinal direction of the surgical tool T at a certain angle (for example, 90 degrees). The cross-sectional positions P1 and P2 in a depth direction are set such that, for example, a surface depth of a retina is situated slightly higher than the lower end of the cross sections.

The controller 104 controls the cross-sectional information acquisition section 1012 to acquire a cross-sectional image of this cross-sectional position P. This makes it possible to easily understand a positional relationship between the tip of a surgical tool and a retina in a cross-sectional image.

(Membrane Processing 2)

Figure 24:
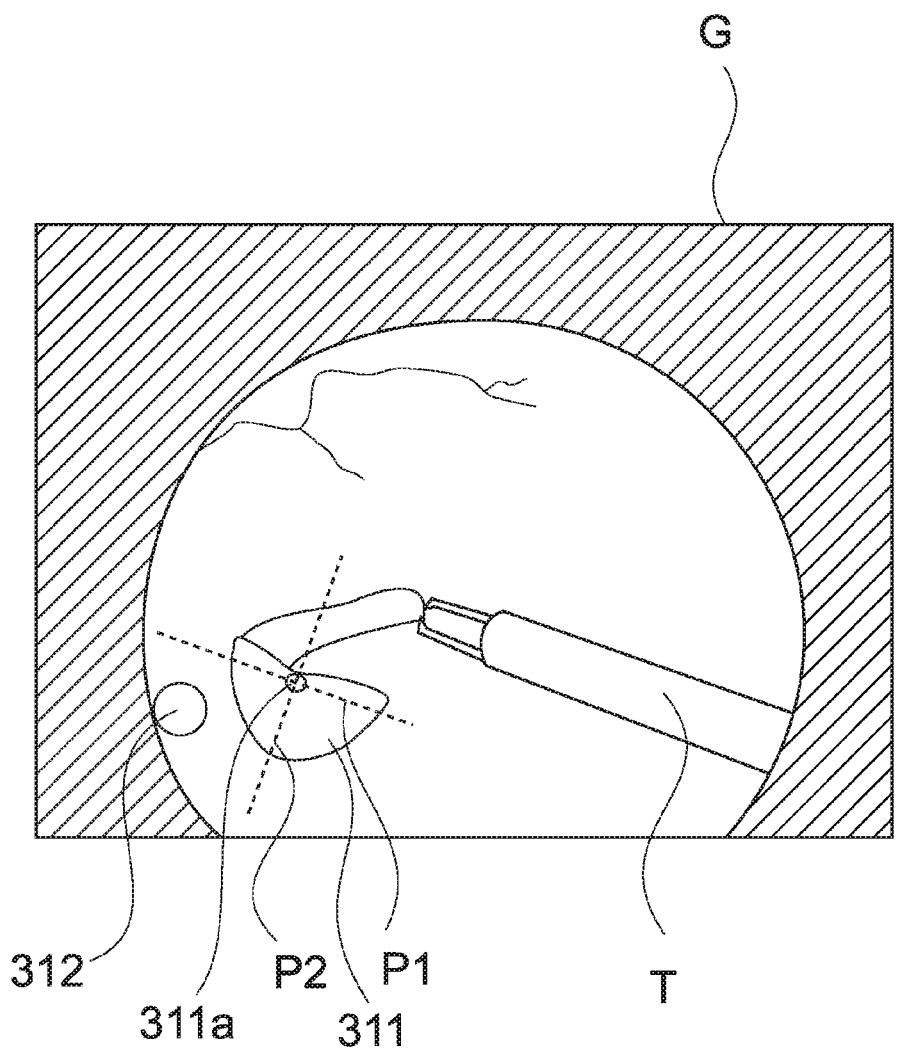
FIG. 24 is a schematic diagram illustrating cross-sectional positions set by the image processing system.

FIG. 24 is a schematic diagram illustrating cross-sectional positions P1 and P2 in a front image G1 when membrane processing is performed. In the membrane processing, there may be a need to constantly gaze at a specific portion (such as a position of a macular region 311). Thus, the controller 104 causes the cross-sectional positions P1 and P2 to follow the tip of a surgical tool using a technique of "Membrane Processing 1" described above, and after the cross-sectional positions P1 and P2 are guided to a position of a gaze target, the controller 104 can fix the cross-sectional positions P1 and P2 at the position of the gaze target (a macular foveal region 311a in the figure) in response to an instruction given using, for example, a foot switch. FIG. 24 illustrates the cross-sectional positions P1 and P2 remaining fixed at the position of the gaze target after the movement of the surgical tool.

(Membrane Processing 3)

Figure 25:
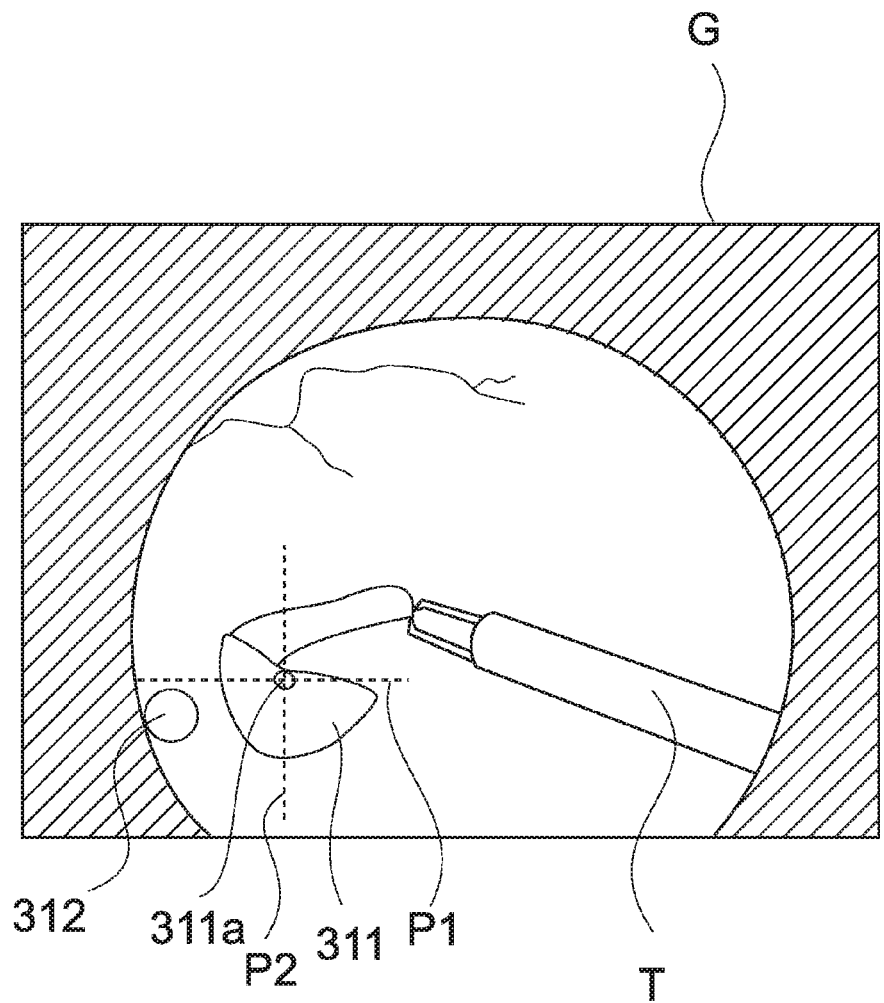
FIG. 25 is a schematic diagram illustrating cross-sectional positions set by the image processing system.

FIG. 25 is a schematic diagram illustrating cross-sectional positions P1 and P2 in a front image G1 when membrane processing is performed. In Membrane Processing 2 described above, there may be a need to perform a fine adjustment of the cross-sectional positions P1 and P2. Thus, the controller 104 can perform a fine adjustment of the positions or the orientations of the cross-sectional positions P1 and P2 in response to an instruction given using, for example, a foot switch. FIG. 25 illustrates an example in which a fine adjustment of the orientations of the cross-sectional positions P1 and P2 is performed from the state illustrated in FIG. 24.

(Membrane Processing 4)

Figure 26:
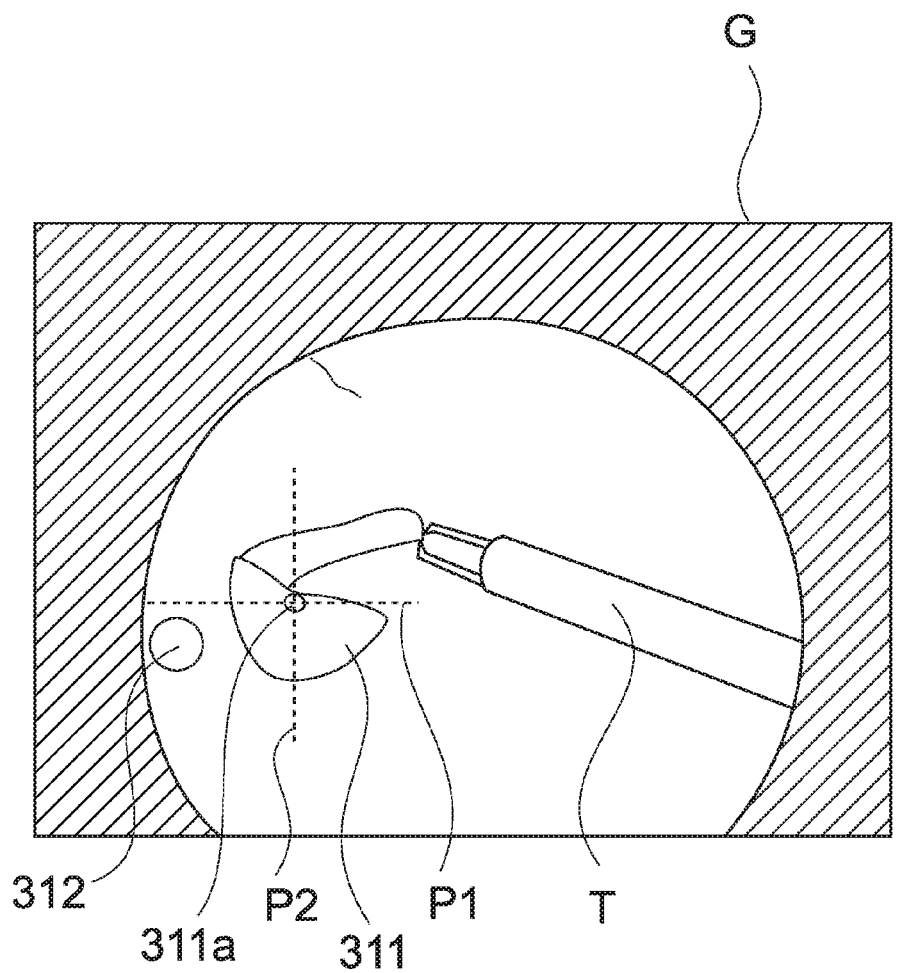
FIG. 26 is a schematic diagram illustrating cross-sectional positions set by the image processing system.

FIG. 26 is a schematic diagram illustrating cross-sectional positions P1 and P2 in a front image G1 when membrane processing is performed. In Membrane Processing 2 or Membrane Processing 3 described above, the cross-sectional positions P1 and P2 may be shifted from a position of a gaze target due to the movement of an eye. Thus, in response to an instruction given using, for example, a foot switch, the controller 104 may perform image processing to track the position of the gaze target, and may cause the cross-sectional positions P1 and P2 to follow the position of the gaze target. FIG. 26 illustrates an example in which the position of the gaze target (the macular region 311) in the front image G is shifted from the state illustrated in FIG. 25 but the cross-sectional positions P1 and P2 move to follow the gaze target.

(Membrane Processing 5)

Figure 27:
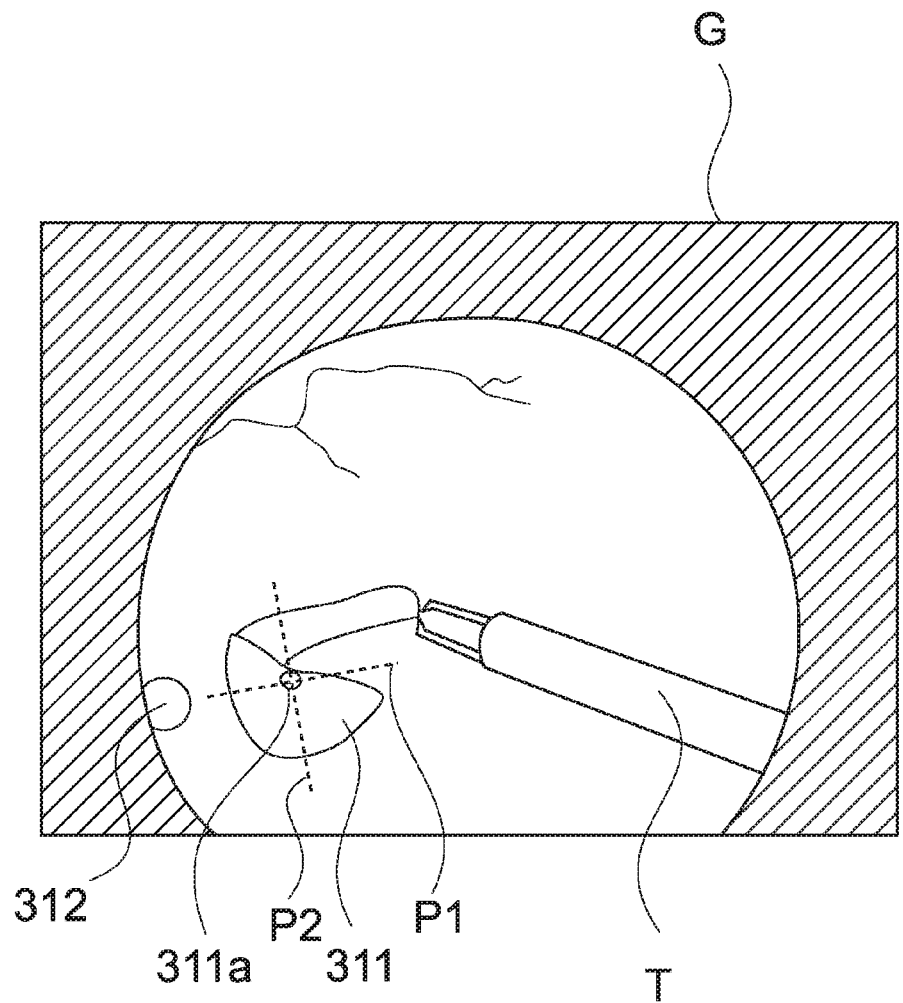
FIG. 27 is a schematic diagram illustrating cross-sectional positions set by the image processing system.

FIG. 27 is a schematic diagram illustrating cross-sectional positions P1 and P2 in a front image G1 when membrane processing is performed. In the membrane processing, it is often the case that the gaze target is a specific site of an eye, such as a macular region or an optic papilla. Thus, in response to an instruction given using, for example, a foot switch, the controller 104 may use the cross-sectional positions P1 and P2 predetermined on the basis of the specific site of an eye. FIG. 27 illustrates an example in which a plane formed by connecting the macular region 311a to the center of an optic papilla 312 is set to be the cross-sectional position P1, and a plane orthogonal to the cross-sectional position P1 is set to be the cross-sectional position P2, the planes being centered on the macular region 311a.

[Surgical Technique: Glaucoma]

(MIGS 1)

Figure 28:
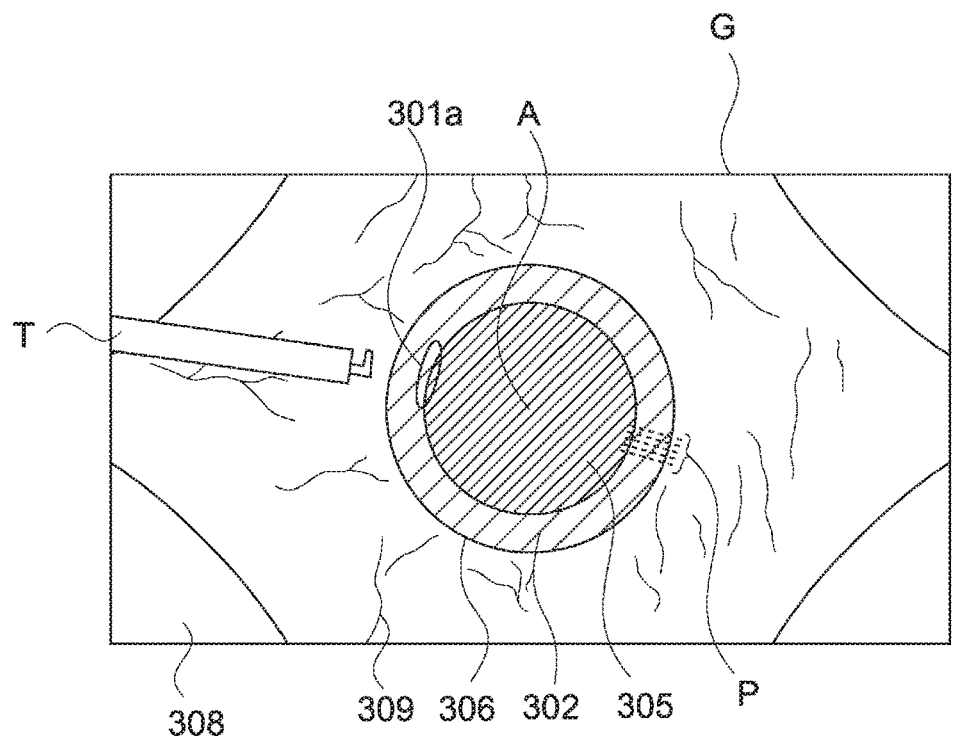
FIG. 28 is a schematic diagram illustrating a cross-sectional position set by the image processing system.

FIG. 28 is a schematic diagram illustrating a cross-sectional position P in a front image G when MIGS is performed. In the MIGS (minimally invasive glaucoma surgery), it is important to grasp a trabecula portion that is a treatment position when, for example, an implant is deployed in a trabecula to create a bypass. An access to the treatment position is made through a wound 301a created diagonally to the trabecula. The controller 104 tracks the position of the wound 301a in advance, and sets the cross-sectional position P near the trabecula situated diagonally to the position of the wound 301a such that small-scale-volume cross-sectional information (volume data constituted of successively captured cross-sectional images) is acquired.

The cross-sectional position P in a depth direction is set such that it is centered at, for example, a height of a trabecula (the iridocorneal angle 307). The controller 104 controls the cross-sectional information acquisition section 1012 to acquire volume data of this cross-sectional position P. This makes it easy to grasp a trabecula portion that is a treatment position.

(MIGS 2)

Figure 29:
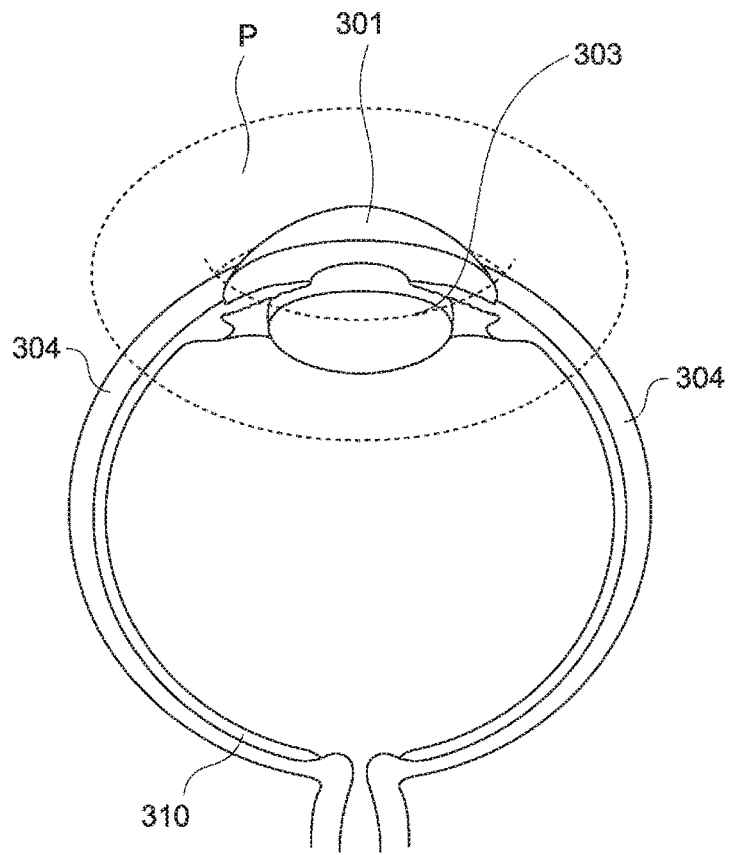
FIG. 29 is a schematic diagram illustrating a range that is set by the image processing system and in which volume data is acquired.

FIG. 29 is a schematic diagram illustrating a relationship between an eye and a volume-data acquisition position when MIGS is performed. In the MIGS, for example, when a procedure to access a wide portion of a trabecula is performed, the controller 104 may acquire volume data in a ring-shaped (such as doughnut-shaped) cross-sectional position P that includes an entire periphery of the trabecula around 360 degrees, as illustrated in FIG. 29.

[Surgical Technique: Descemet's Stripping Automated Endothelial Keratoplasty]
(DSAEK)

Figure 30:
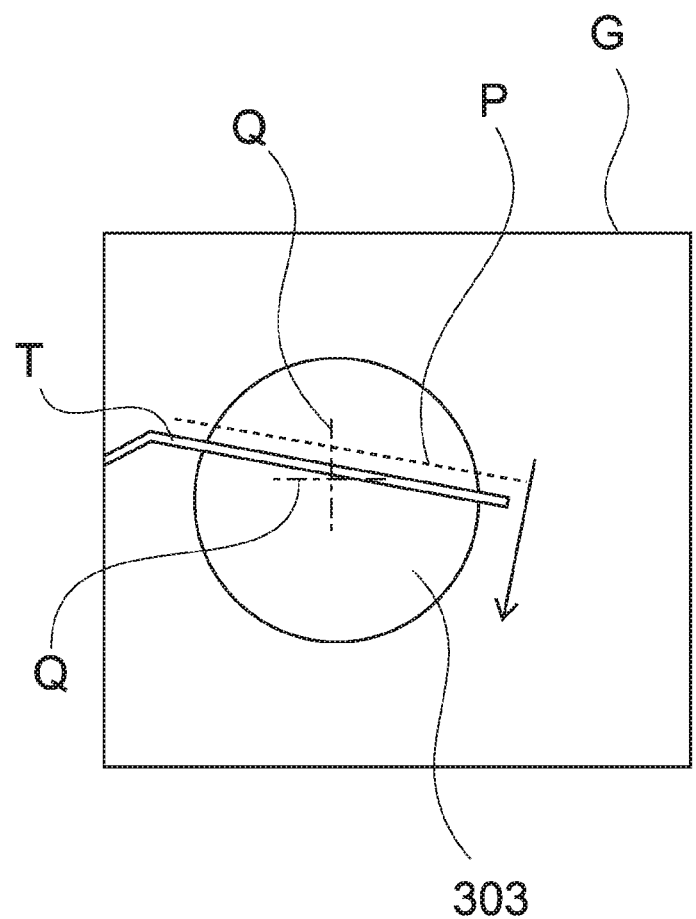
FIG. 30 is a schematic diagram illustrating a cross-sectional position set by the image processing system.
Figure 31:
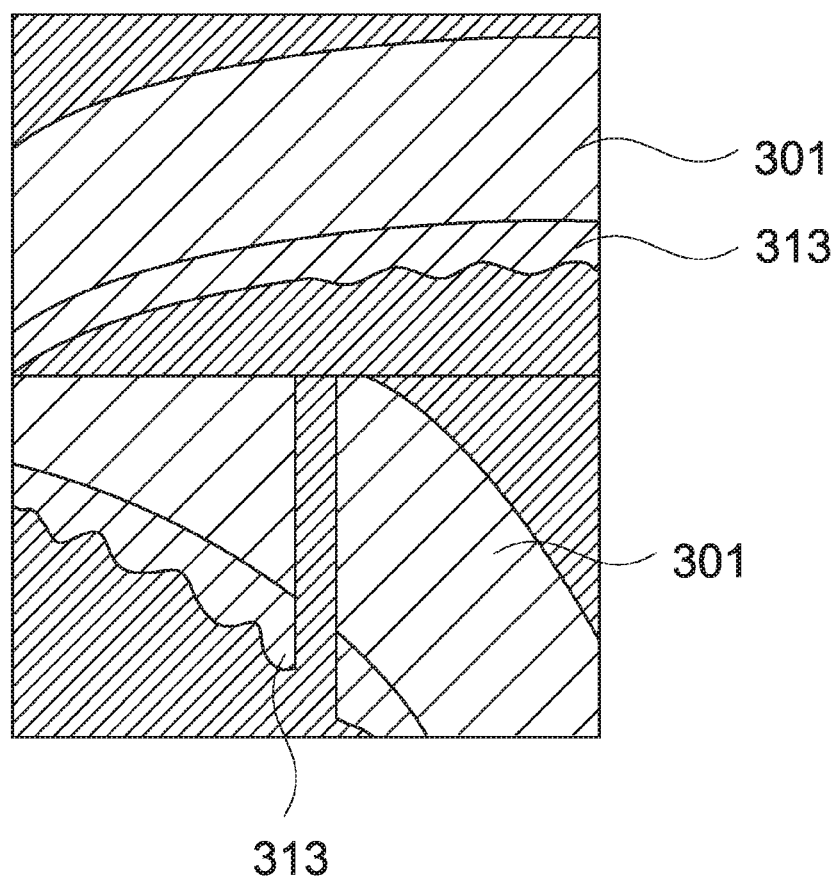
FIG. 31 illustrates a general cross-sectional image when a specific surgical technique is performed.

FIG. 30 is a schematic diagram illustrating a cross-sectional position P in a front image G when DSAEK is performed. As illustrated in the figure, in the DSAEK (Descemet's stripping automated endothelial keratoplasty), when an implant is implanted in a patient, a space between the cornea of the patient and the implant is gradually reduced by brushing the space using a bar-shaped surgical tool T, and it is necessary to confirm a portion that has been brushed, in order to confirm whether the space has disappeared. In the figure, the movement direction of the surgical tool T is indicated by an arrow. FIG. 31 illustrates an example of a cross-sectional image acquired in a general fixed cross section (a cross-sectional position Q in FIG. 30), and includes the cornea 301 and an implant 313.

As illustrated in FIG. 30, the controller 104 sets, to be the cross-sectional position P, a position that is parallel to the bar-shaped surgical tool T and is situated away from the bar-shaped surgical tool T in a direction of being slightly less advanced than the surgical tool T. The cross-sectional position P in a depth direction is set such that, for example, the position of the top of an inner surface of a cornea (in FIG. 4, an uppermost point in the upwardly convex portion) is situated slightly lower than the upper end in a cross-sectional image. The controller 104 controls the cross-sectional information acquisition section 1012 to acquire a cross-sectional image of this cross-sectional position P. This makes it easy to confirm a space between a cornea and an implant in a cross-sectional image.

(Determination of Scale According to Magnification of Microscope)

Figure 32:
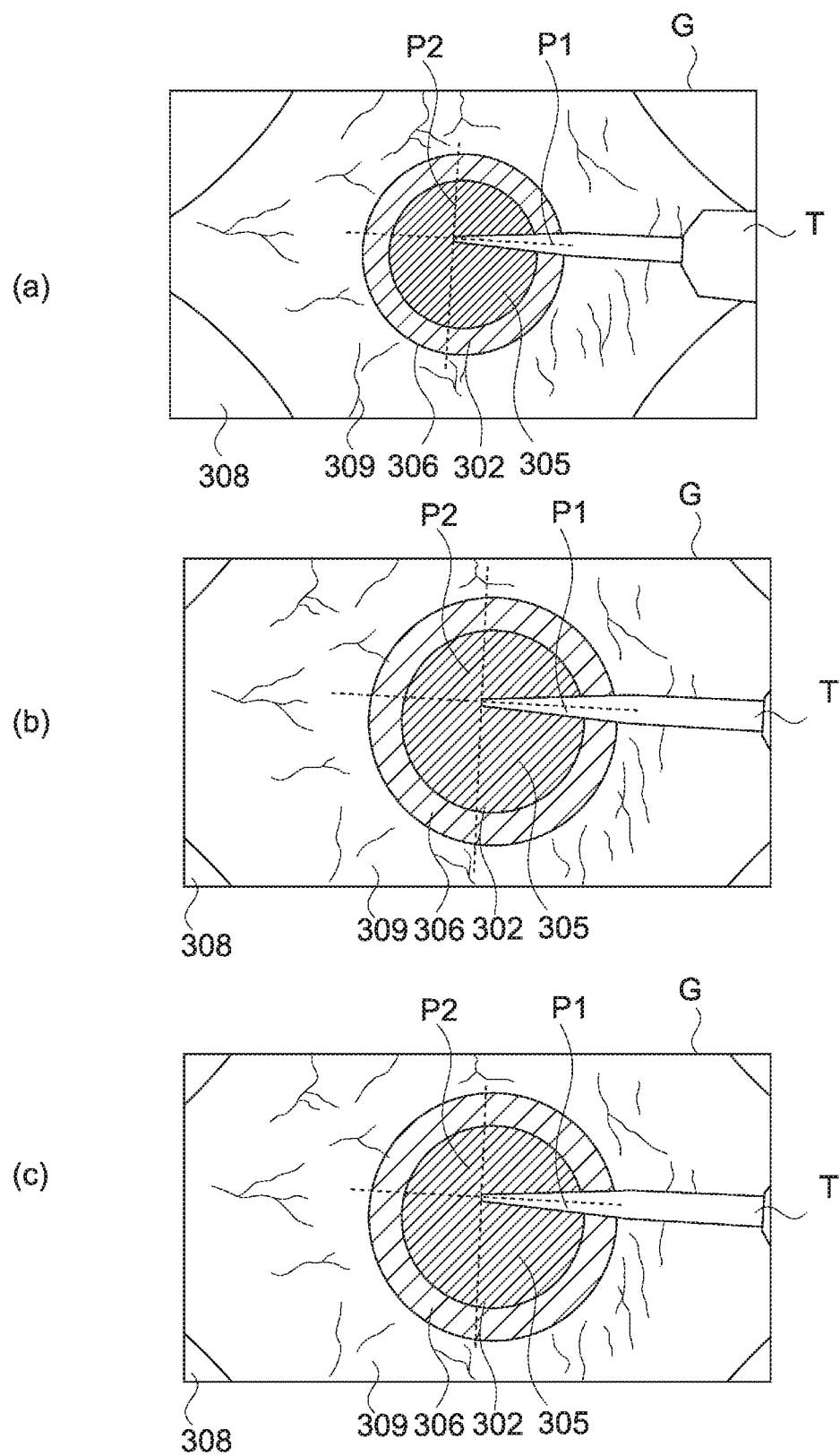
FIG. 32 is a schematic diagram illustrating cross-sectional positions set by the image processing system.

When the magnification of a microscope for the front image acquisition section 1011 is changed, the controller 104 may adjust the cross-sectional position P according to the magnification. FIG. 32 is a schematic diagram illustrating an adjustment of cross-sectional positions P1 and P2. When the magnification of a microscope is made higher from (a) of FIG. 32 to (b) of FIG. 32, the controller 104 can adjust the scale such that the range occupied by the cross-sectional positions P1 and P2 in a front image G remains unchanged. Further, as illustrated in (c) of FIG. 32, the controller 104 may adjust the scale of the cross-sectional positions P1 and P2 such that the range occupied by the cross-sectional positions P1 and P2 with respect to an image frame in the front image G remains unchanged.

(Filter)

A result of detecting the tip of a surgical tool or a site of an eye may vary slightly in a temporal direction due to an error. Further, the movement of, for example, the tip of a surgical tool may vary discontinuously. In the cases described above, the controller 104 can prevent the occurrence of variation of a cross-sectional position P by applying a smoothing filter in a temporal direction to a position to detect, for example, the tip of a surgical tool. Regarding turning the filter on or off, selection may be performed using a menu display as illustrated in FIG. 7 and FIG. 10, or using, for example, a foot switch.

<Regarding Presentation of Cross-Sectional Acquisition Position>

(Presentation of Cross-Sectional Acquisition Position in Front Image)

As described above, the display information generator 105 superimposes a cross-sectional position on a front image by being controlled by the controller 104, and generates display information. A cross-sectional line indicating a cross-sectional position may be displayed on a front image (refer to FIG. 9), as described above, but such a line may reduce the visibility of a surgical field. Thus, as illustrated in FIG. 33, the display information generator 105 may superimpose, near an end point of a cross-sectional line, an image R indicating a cross-sectional position. The image R may have a shape of an arrow, as illustrated in the figure, or may have a shape other than that of an arrow.

Figure 34:
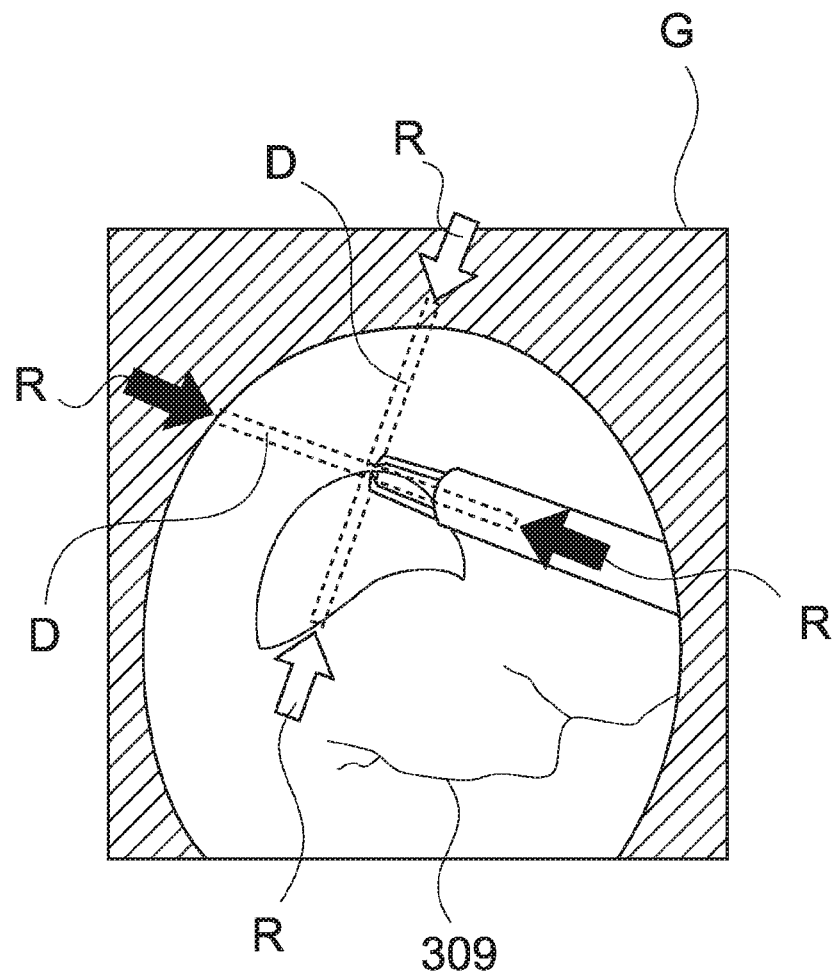
FIG. 34 schematically illustrates the image indicating the cross-sectional position presented by the image processing system.

Further, in addition to displaying the image R, the display information generator 105 can set, to be achromatic, a range D corresponding to the cross-sectional line in the front image, as illustrated in FIG. 34. Conversely, the display information generator 105 may only set the range D to be chromatic and set a region other than the range D to be achromatic. Moreover, the display information generator 105 can indicate a cross-sectional position by using different image processing methods for the range D and the region other than the range D. Examples of the image processing method include changing the level of a saturation of color or the level of brightness.

(Presentation of Depth of Cross-Sectional Position)

The display information generator 105 can generate display information that indicates the depth of a cross-sectional position. FIGS. 35 and 36 illustrate examples of images indicating the depth of a cross-sectional position. As illustrated in FIG. 35, the display information generator 105 can linearly depict a relative depth of a cross section by placing an indicator B in an image including an eye (for example, the schematic diagram). Further, as illustrated in FIG. 36, the display information generator 105 can also depict a relative position of a cross section in an image including an eye (for example, the schematic diagram) using a shape C.

<Regarding Presentation of Cross-Sectional Information>

Figure 37:
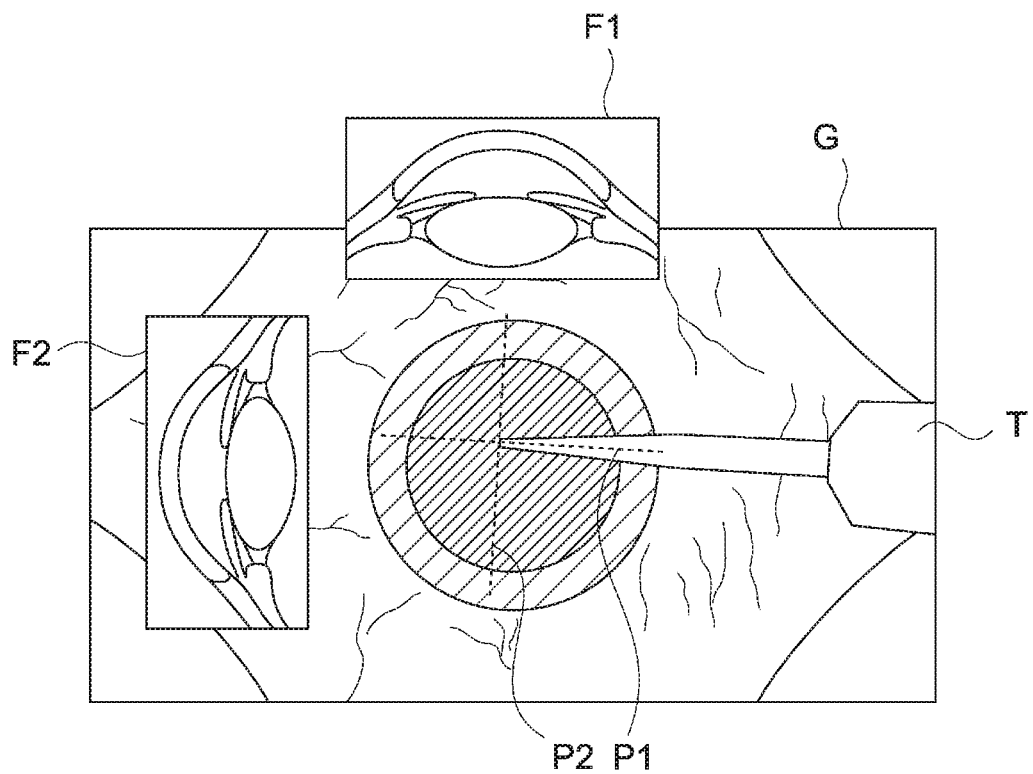
FIG. 37 schematically illustrates display information presented by the image processing system.
Figure 38:
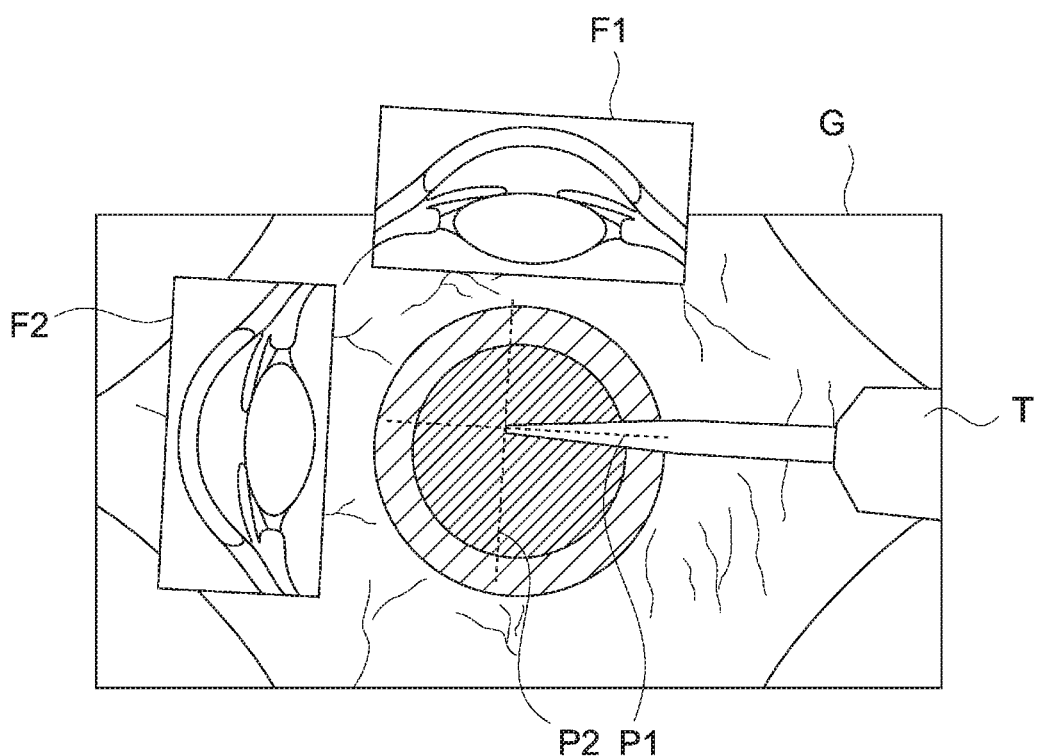
FIG. 38 schematically illustrates display information presented by the image processing system.

The display information generator 105 can generate an image including a front image and a cross-sectional image as display information. FIGS. 37 to 39 illustrate an image including a front image G, a cross-sectional image F1, and a cross-sectional image F2. The cross-sectional image F1 is a cross-sectional image acquired at a cross-sectional position P1, and the cross-sectional image G2 is a cross-sectional image acquired at a cross-sectional position P2.

(General Presentation Method)

As illustrated in FIG. 37, a cross-sectional image is generally arranged not depending on the position or the orientation of a cross section, but at a fixed position at a fixed angle (in many cases, vertically or horizontally to the periphery of an image).

(Reflection of Orientation of Cross Section)

As illustrated in FIG. 38, the display information generator 105 aligns the orientation of a cross section with the orientation of a cross-sectional image (set the periphery of the cross-sectional position P1 to be parallel with the periphery of the cross-sectional image F1, and set the periphery of the cross-sectional position P2 to be parallel with the periphery of the cross-sectional image F2), and this makes it possible to easily understand a correspondence relationship between a cross-sectional position and a cross-sectional image.

(Reflection of Position of Cross Section)

Figure 40:
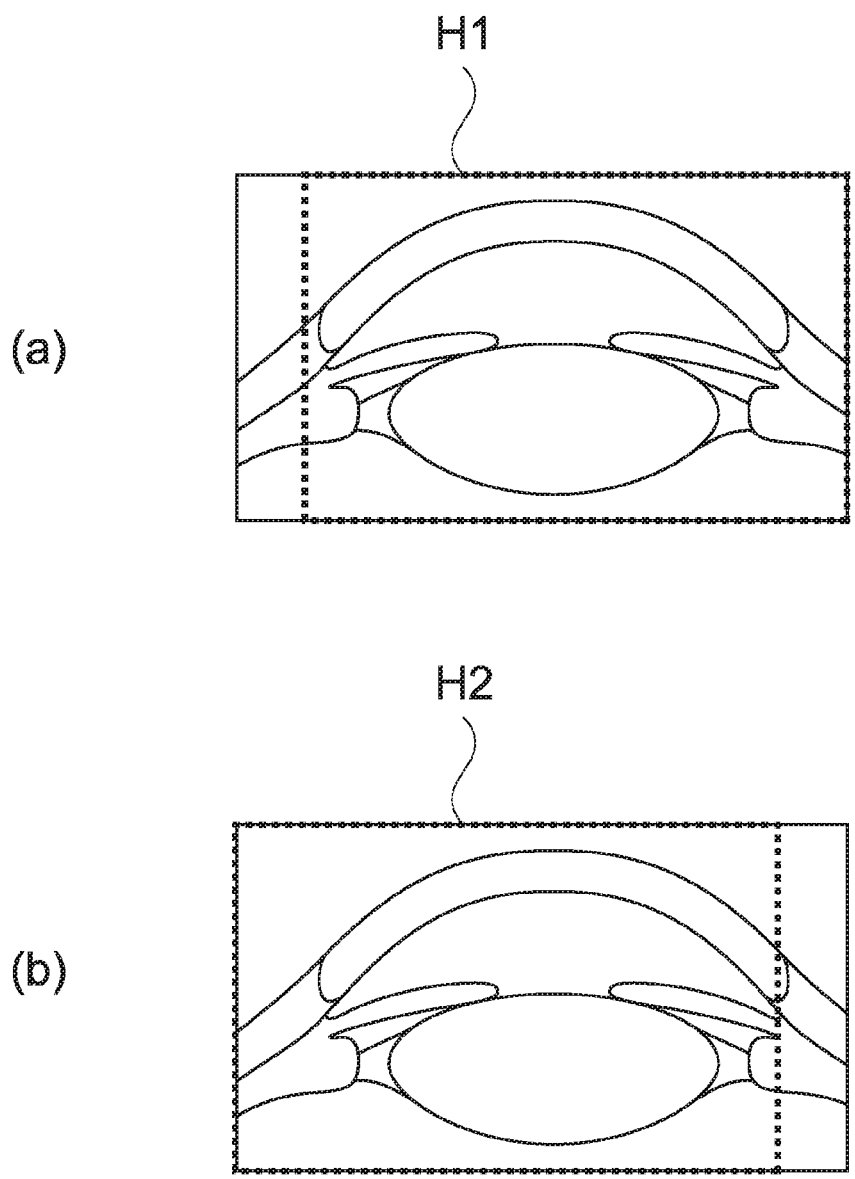
FIG. 40 is a schematic diagram illustrating a range in which cross-sectional information is acquired by the image processing system.

Further, FIG. 40 is a schematic diagram illustrating a range of a cross-sectional image arranged in display information. A range H1 illustrated in (a) of FIG. 40 is a range acquired as the cross-sectional image F1 illustrated in (a) of FIG. 39, and a range H2 illustrated in (b) of FIG. 40 is a range acquired as the cross-sectional image F1 illustrated in (b) of FIG. 39.

The controller 104 causes the cross-sectional information acquisition section 1012 to acquire a cross-sectional image in the range H1 at a cross-sectional position P1 according to the position of the tip of the surgical tool T, as illustrated in (a) of FIG. 40. After that, when the position of the tip of the surgical tool T moves, the controller 104 causes the cross-sectional information acquisition section 1012 to acquire a cross-sectional image in the range H2 at the cross-sectional position P1, as illustrated in (b) of FIG. 40. For example, the display information generator 105 moves the position to present a cross-sectional image F1 in a front image G according to the position of the cross-sectional position P1 in the longitudinal direction of the surgical tool. For example, when a surgical tool moves forward in its longitudinal direction as in the case of the change from (a) of FIG. 39 to (b) of FIG. 39, the display information generator 105 moves the position to present the cross-sectional image F1 to the left in the front image G by a distance that the surgical tool moves forward.

This enables the display information generator 105 to present a moving image of a cross-sectional image in which a cross-sectional image F1 at a cross-sectional position P1 that extends in the longitudinal direction of a surgical tool T appears to be a portion of a large cross-sectional image, the portion being extracted and presented in a window. For example, in formation of an incision in PEA, when the method for acquiring a cross-sectional image described using FIG. 19 is changed to a method for acquiring a cross-sectional image in a range at a certain distance from a position of the tip of a surgical tool only with respect to a range in which a cross section is acquired, and when the method uses the presentation method described in FIG. 40, this makes it possible to acquire sufficient information even if a range in which a cross section is acquired in the longitudinal direction of a surgical tool, is made smaller.

Figure 41:
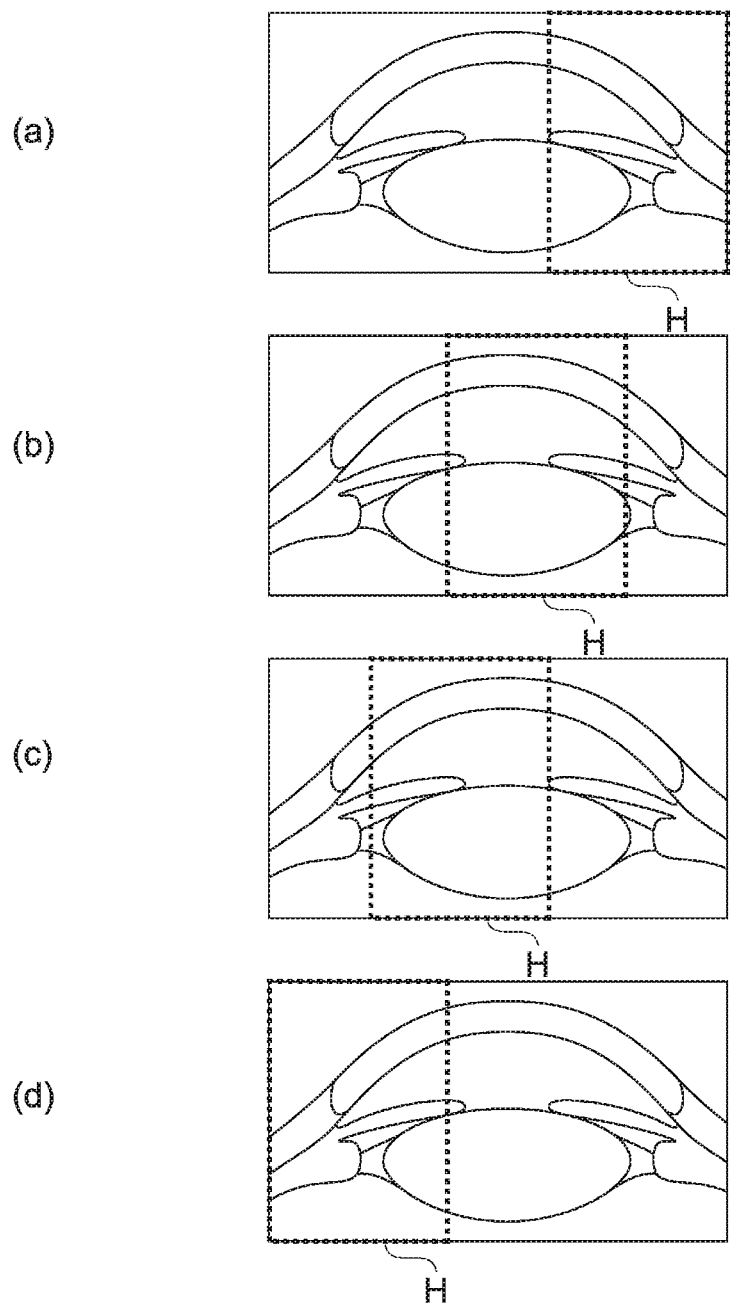
FIG. 41 is a schematic diagram illustrating a range in which cross-sectional information is acquired by the image processing system.

This results in being able to temporally increase the number of cross-sections acquired, and to perform a temporally intensive observation. This effect becomes greater when a range H in which a cross-sectional image is acquired is made smaller, as illustrated in FIG. 41.

(DSAEK 1)

As described in FIGS. 30 and 31, in the DSAEK, when using the method for acquiring cross-sectional information in the procedure of removing a space between the cornea of a patient and an implant, an operator may wish to confirm a state of the space after the operator determines that he/she could sufficiently reduce the space. FIG. 42 schematically illustrates a moving image displayed as display information. For example, the controller 104 holds cross-sectional images acquired by the method described above with respect to a final piece of brushing, as illustrated in FIG. 42, from among brushing of a cornea performed using a surgical tool in the procedure, and the display information generator 105 can play it back as a moving image. This enables an operator to easily confirm a state of a space.

(DSAEK 2)

(a) of FIG. 43 illustrates an example of volume data acquired by the cross-sectional information acquisition section 1012, and (b) of FIG. 43 illustrates an example of a cross-sectional image generated from the volume data. Likewise, the controller 104 holds cross-sectional images regarding a final piece of brushing, and can generate volume data illustrated in (a) of FIG. 43 using the cross-sectional images. Further, as illustrated in (b) of FIG. 43, the controller 104 displays an arbitrary cross-sectional image from among the volume data, for example, in accordance with an instruction given by an operator, and this enables the operator to easily confirm a state of a space.

<Additional Note>

(Prediction of Depth Position)

The controller 104 can obtain the depth of the tip of a surgical tool using the position of the tip of the surgical tool in a cross-sectional image, but when the tip of the surgical tool is not included in the cross-sectional image, the controller 104 can also obtain the depth by performing prediction using, for example, the movement of the position of the tip in a cross-sectional image in the past. The controller 104 may use, as a current depth of the tip of a surgical tool, the depth of the tip of the surgical tool obtained the last time the tip of the surgical tool exists in a cross-sectional image, or may perform prediction considering, for example, a speed in a depth direction.

With respect to the depth of each site of an eye, the controller 104 can use the depth of a certain site if the certain site exists in a cross-sectional image. When the certain site does not exist in the cross-sectional image, the controller 104 can also obtain the depth of the certain site using, for example, a prediction from the depth of the certain site in the past, or a prediction from the depth of another site existing in the cross-sectional image and from a relationship in depth between the other site and the certain site (such as an actual measurement in a cross-sectional image, measurement before surgery, and a commonly used average). Examples of the site of an eye favorably used as a depth reference include a corneal vertex, an iridocorneal angle, a vertex of an anterior capsule, a vertex of a posterior capsule, a retina, a choroid, and a sclera.

(Setting of Scanning Parameter)

As described in FIG. 16, when the controller 104 scans the cross-sectional position, the controller 104 can change, for example, an offset of a scanning position (such as the center) as needed before and during surgery in response to a manipulation input performed by a user, the offset of a scanning position being an offset of a scanning position from the tip of a surgical tool or from a specific site of an eye such as a corneal limbus. Further, the controller 104 can also change a length of scanning as needed before and during surgery in response to a manipulation input performed by a user.

(Use of Analogous Reference Position)

The cornea's center described above may be replaced by a pupil's center.

(Purpose of Using Cross-Sectional Information)

In the descriptions above, an acquired cross section is primarily used to perform presentation to a user, but it can also be used for other purposes such as detecting a risk from cross-sectional information.

(Method for Designating Operation Mode)

In principle, the selection of an operation mode in the image processing system 100 is selecting an operation mode corresponding to a procedure selected by the controller 104, as described above. Further, the image processing system 100 may have a configuration that enables a user to directly designate an operation mode, or may have a configuration that makes it possible to directly separately designate, for example, a method for acquiring a cross section, a method for presenting a cross-sectional position, and a method for presenting a cross-sectional image.

<Hardware Configuration>

Figure 44:
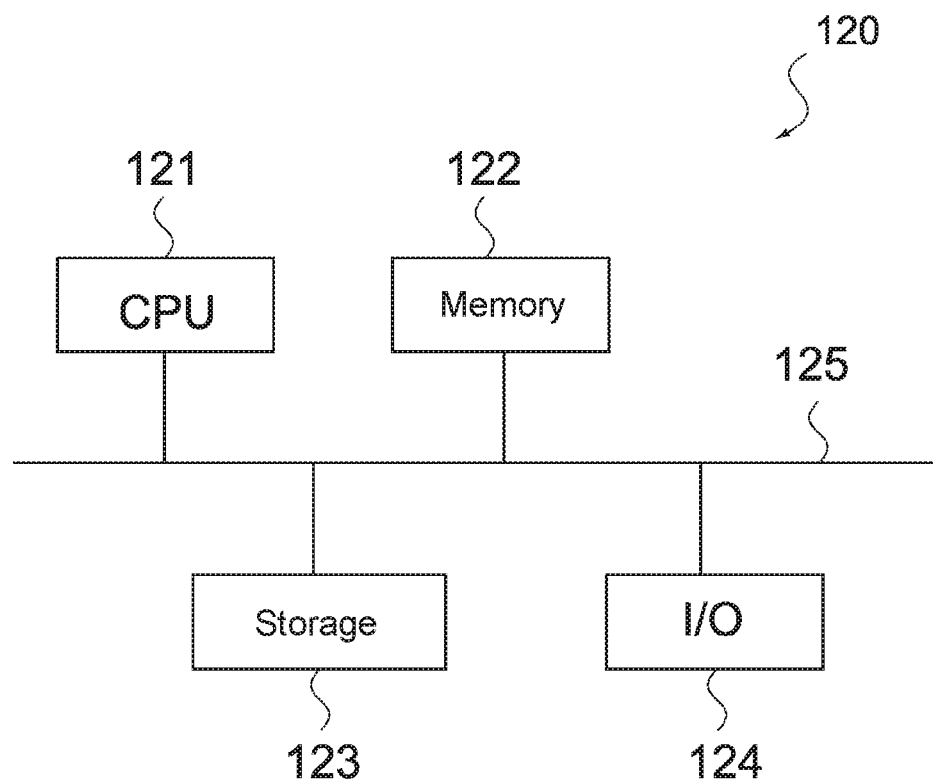
FIG. 44 schematically illustrates a hardware configuration of an image processing device included in the image processing system.

FIG. 44 schematically illustrates a hardware configuration of the image processing device 120. As illustrated in the figure, the image processing device 120 includes, as the hardware configuration, a CPU 121, a memory 122, a storage 123, and an input/output section (I/O) 124. They are connected to one another through a bus 125.

The CPU (central processing unit) 121 controls other components in accordance with a program stored in the memory 122, and performs data processing in accordance with the program and stores a result of the processing in the memory 122. The CPU 121 may be a microprocessor.

The memory 122 stores therein the program executed by the CPU 121, and data. The memory 122 may be a random access memory (RAM).

The storage 123 stores therein a program and data. The storage 123 may be a hard disk drive (HDD) or a solid state drive (SSD).

The input/output section (I/O) 124 receives an input to the image processing device 120, and provides an output from the image processing device 120 to the outside. The input/output section (I/O) 124 includes an input device such as a keyboard or a mouse, an output device such as a display, and a connection interface such as a network.

The hardware configuration of the image processing device 120 is not limited to what has been described above, and it is sufficient if it can provide a functional configuration of the image processing device 120. Further, a portion of or all of the hardware configuration may exist on a network.

Note that the present technology may also take the following configurations.

(1) An image processing device including:
   an image recognition section that performs an image recognition with respect to a front image that is a captured image of an eye;
   a display information generator that generates display information; and
   a controller that controls at least one of a cross-sectional information acquisition section or the display information generator according to a selected procedure, the cross-sectional information acquisition section acquiring cross-sectional information regarding a cross section of an eye.
(2) The image processing device according to (1), in which the controller selects a procedure in response to an instruction given by a user.
(3) The image processing device according to (1), in which the controller selects a procedure according to an instruction given by a user and a state recognition performed with respect to the front image.
(4) The image processing device according to (1), in which the controller selects a procedure according to a state recognition performed with respect to the front image.
(5) The image processing device according to (2) or (3), in which
   the controller determines the instruction given by the user using a result of a recognition performed by the image recognition section.
(6) The image processing device according to (3) or (4), in which
   the image processing device according to claim 3 or 4, wherein
   the controller performs a state recognition using a result of a recognition performed by the image recognition section.
(7) The image processing device according to (5), in which
   the image recognition section recognizes a surgical tool included in the front image, and
   the controller determines the instruction given by the user according to a position of a tip of the surgical tool included in the front image.
(8) The image processing device according to (6), in which
   the image recognition section recognizes a surgical tool included in the front image, and
   the controller specifies a type of the surgical tool included in the front image, and performs the state recognition according to the type of the surgical tool.
(9) The image processing device according to (8), in which
   the controller performs the state recognition according to the type of the surgical tool and characteristics of the front image.
(10) The image processing device according to any one of (1) to (9), in which
   the image recognition section recognizes a surgical tool included in the front image, and
   the controller determines a cross-sectional position according to a shape of the surgical tool included in the front image, the cross-sectional position being a position of a cross section for which cross-sectional information is to be acquired.
(11) The image processing device according to any one of (1) to (9), in which
   the image processing device according to claim 1, wherein
   the image recognition section recognizes a site of an eye that is included in the front image, and
   the controller determines a cross-sectional position according to the site of an eye included in the front image, the cross-sectional position being a position of a cross section for which cross-sectional information is to be acquired.
(12) The image processing device according to any one of (1) to (9), in which
   the image recognition section recognizes a surgical tool and a site of an eye that are included in the front image, and
   the controller determines a cross-sectional position according to a shape of the surgical tool included in the front image and the site of an eye included in the front image, the cross-sectional position being a position of a cross section for which cross-sectional information is to be acquired.
(13) The image processing device according to any one of (1) to (12), in which
   the display information generator generates the display information including the cross-sectional information acquired by the cross-sectional information acquisition section, and changes a position of the cross-sectional information in the display information according to a cross-sectional position that is a position of a cross section for which cross-sectional information is to be acquired.
(14) The image processing device according to any one of (1) to (13), in which
   the display information generator generates the display information including the cross-sectional information acquired by the cross-sectional information acquisition section, and changes an orientation of the cross-sectional information in the display information according to an orientation of a cross section for which cross-sectional information is to be acquired.
(15) The image processing device according to any one of (1) to (14), in which
   the image processing device according to claim 1, wherein
   the image recognition section performs an image recognition with respect to the cross-sectional information, and the controller detects an incision edge formed by a treatment performed according to a result of the image recognition performed by the image recognition section with respect to the cross-sectional information.

(16) The image processing device according to (15), in which the image recognition section recognizes a site of an eye in the front image, the controller specifies a position of the incision edge in the front image according to the site of an eye detected by performing the image recognition, and the display information generator generates display information obtained by superimposing an image at the position specified by the controller, the superimposed image including the incision edge.

(17) The image processing device according to any one of (1) to (16), in which the display information generator generates display information obtained by superimposing an image on the front image, the superimposed image indicating an end point of a cross-sectional line indicating a position of a cross section for which cross-sectional information is to be acquired.

(18) The image processing device according to any one of (1) to (17), in which the display information generator generates display information obtained by processing the front image to depict a cross-sectional line indicating a position of a cross section for which cross-sectional information is to be acquired.

(19) An image processing method including:

performing, by an image recognition section, an image recognition with respect to a front image that is a captured image of an eye;

generating display information by a display information generator; and controlling, by a controller, at least one of a cross-sectional information acquisition section or the display information generator according to a selected procedure, the cross-sectional information acquisition section acquiring cross-sectional information regarding a cross section of an eye.

(20) An image processing system including:

a cross-sectional information acquisition device that includes a cross-sectional information acquisition section that generates cross-sectional information regarding a cross section of an eye;

a front image capturing device that includes a front image acquisition section that captures an image of an eye to generate a front image, and an image processing device that includes an image recognition section, a display information generator, and a controller, the image recognition section performing an image recognition with respect to the front image, the display information generator generating display information, the controller controlling at least at least one of the cross-sectional information acquisition section or the display information generator according to a selected procedure.

REFERENCE SIGNS LIST 100 image processing system
101 image information acquisition section
102 image recognition section
103 interface
104 controller
105 display information generator
106 display section
1011 front image acquisition section
1012 cross-sectional information acquisition section

The invention claimed is:

1. An image processing device comprising:
circuitry configured to perform an image recognition with respect to a front image that is a captured image of an eye;
generate display information; and
control at least one of a cross-sectional information acquisition section or the generation of the display information according to a selected procedure, the cross-sectional information acquisition section acquiring cross-sectional information regarding a cross section of the eye, wherein
the display information includes a menu,
the menu comprises a two-level menu in which a first level indicates a disease and a second level indicates a procedure to treat the disease, and
in response to an instruction given by a user through the menu, the circuitry selects the procedure and a cross-sectional image for the procedure.

2. The image processing device according to claim 1, wherein the circuitry is configured to select the procedure according to the instruction given by the user and a state recognition performed with respect to the front image.

3. The image processing device according to claim 2, wherein the circuitry is configured to perform the state recognition using a result of the image recognition.

4. The image processing device according to claim 3, wherein
the circuitry is configured to
recognize a surgical tool included in the front image,
specify a type of the surgical tool included in the front image, and
perform the state recognition according to the type of the surgical tool.

5. The image processing device according to claim 4, wherein
the circuitry is configured to perform the state recognition according to the type of the surgical tool and characteristics of the front image.

6. The image processing device according to claim 1, wherein the circuitry is configured to select the procedure according to a state recognition performed with respect to the front image.

7. The image processing device according to claim 1, wherein, the circuitry is configured to determine the instruction given by the user using a result of the image recognition.

8. The image processing device according to claim 7, wherein
the circuitry is configured to
recognize a surgical tool included in the front image, and
determine the instruction given by the user according to a position of a tip of the surgical tool included in the front image.

9. The image processing device according to claim 1, wherein
the circuitry is configured to
recognize a surgical tool included in the front image, and
determine a cross-sectional position according to a shape of the surgical tool included in the front image, the cross-sectional position being a position of the cross section for which the cross-sectional information is to be acquired.

10. The image processing device according to claim 1, wherein
the circuitry is configured to
recognize a site of the eye that is included in the front image, and
determine a cross-sectional position according to the site of the eye included in the front image, the cross-sectional position being a position of the cross section for which the cross-sectional information is to be acquired.

11. The image processing device according to claim 1, wherein
the circuitry is configured to
recognize a surgical tool and a site of the eye that are included in the front image, and
determine a cross-sectional position according to a shape of the surgical tool included in the front image and the site of the eye included in the front image, the cross-sectional position being a position of the cross section for which the cross-sectional information is to be acquired.

12. The image processing device according to claim 1, wherein
the circuitry is configured to
generate the display information including the cross-sectional information acquired by the cross-sectional information acquisition section, and
change a position of the cross-sectional information in the display information according to a cross-sectional position that is a position of the cross section for which the cross-sectional information is to be acquired.

13. The image processing device according to claim 1, wherein
the circuitry is configured to
generate the display information including the acquired cross-sectional information, and
change an orientation of the cross-sectional information in the display information according to an orientation of the cross section for which the cross-sectional information is to be acquired.

14. The image processing device according to claim 1, wherein
the circuitry is configured to
perform an image recognition with respect to the cross-sectional information, and
detect an incision edge formed by a treatment performed according to a result of the image recognition performed with respect to the cross-sectional information.

15. The image processing device according to claim 14, wherein
the circuitry is configured to
recognize a site of the eye in the front image,
specify a position of the incision edge in the front image according to the site of the eye detected by performing the image recognition, and
generate display information obtained by superimposing an image at the specified position, the superimposed image including the incision edge.

16. The image processing device according to claim 1, wherein
the circuitry is configured to generate display information obtained by superimposing an image on the front image, the superimposed image indicating an end point of a cross-sectional line indicating a position of the cross section for which the cross-sectional information is to be acquired.

17. The image processing device according to claim 1, wherein
the circuitry is configured to generate display information obtained by processing the front image to depict a cross-sectional line indicating a position of the cross section for which the cross-sectional information is to be acquired.

18. An image processing method comprising:
performing, by circuitry, an image recognition with respect to a front image that is a captured image of an eye;
generating display information by the circuitry, wherein the display information includes a menu comprising a two-level menu in which a first level indicates a disease and a second level indicates a procedure to treat the disease;
controlling, by the circuitry, at least one of a cross-sectional information acquisition or the generation of the display information according to a selected procedure, the cross-sectional information acquisition acquiring cross-sectional information regarding a cross section of the eye; and
in response to an instruction given by a user through the menu, selecting, by the circuitry, the procedure and a cross-sectional image for the procedure.

19. An image processing system comprising:
a cross-sectional information acquisition device that includes circuitry configured to generate cross-sectional information regarding a cross section of an eye;
an image capturing device that includes circuitry configured to capture an image of the eye to generate a front image, and
an image processing device that includes circuitry configured to
perform an image recognition with respect to the front image,
generate display information, and
control at least at least one of the cross-sectional information acquisition or the generation of the display information according to a selected procedure, wherein
the display information includes a menu,
the menu comprises a two-level menu in which a first level indicates a disease and a second level indicates a procedure to treat the disease, and
in response to an instruction given by a user through the menu, the circuitry of the image processing device selects the procedure and a cross-sectional image for the procedure.

* * * * *